United States Patent
Bai et al.

(10) Patent No.: US 9,926,268 B2
(45) Date of Patent: Mar. 27, 2018

(54) METHOD FOR PREPARING AZETIDINONE COMPOUND AND INTERMEDIATE OF AZETIDINONE COMPOUND

(71) Applicant: Zhejiang Hisun Pharmaceutical Co., Ltd., Taizhou (CN)

(72) Inventors: Hua Bai, Taizhou (CN); Xuyang Zhao, Chengdu (CN); Yuncai Zhang, Taizhou (CN); Xufei Li, Taizhou (CN); Yong Zhang, Zhejiang (CN); Dezhou Xu, Taizhou (CN); Li Zhang, Taizhou (CN); Xiaojie Xu, Taizhou (CN); Qifeng Zhu, Taizhou (CN); Xiaoming Wang, Taizhou (CN); Zhiqing Yang, Taizhou (CN); Zehua Zhong, Taizhou (CN); Jian Zhang, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 15/317,297

(22) PCT Filed: Jun. 5, 2015

(86) PCT No.: PCT/CN2015/080893
§ 371 (c)(1),
(2) Date: Dec. 8, 2016

(87) PCT Pub. No.: WO2015/188727
PCT Pub. Date: Dec. 17, 2015

(65) Prior Publication Data
US 2017/0121281 A1    May 4, 2017

(30) Foreign Application Priority Data

Jun. 9, 2014    (CN) .......................... 2014 1 0251262

(51) Int. Cl.
| | |
|---|---|
| C07C 51/367 | (2006.01) |
| C07C 67/327 | (2006.01) |
| C07D 205/08 | (2006.01) |
| C07C 67/30 | (2006.01) |
| C07C 67/343 | (2006.01) |
| C07C 69/65 | (2006.01) |
| C07C 69/732 | (2006.01) |
| C07C 59/56 | (2006.01) |

(52) U.S. Cl.
CPC .......... *C07D 205/08* (2013.01); *C07C 51/367* (2013.01); *C07C 59/56* (2013.01); *C07C 67/30* (2013.01); *C07C 67/327* (2013.01); *C07C 67/343* (2013.01); *C07C 69/65* (2013.01); *C07C 69/732* (2013.01)

(58) Field of Classification Search
CPC ............................ C07C 51/367; C07C 67/327
See application file for complete search history.

(56) References Cited

U.S. PATENT DOCUMENTS

| | | | |
|---|---|---|---|
| 5,688,990 A | 11/1997 | Shankar | |
| 5,789,413 A * | 8/1998 | Black | .................... C07C 311/29 514/183 |
| 5,846,966 A | 12/1998 | Rosenblum et al. | |

(Continued)

FOREIGN PATENT DOCUMENTS

| | | |
|---|---|---|
| CN | 1144522 A | 3/1997 |
| WO | 2011017907 A1 | 2/2011 |

(Continued)

OTHER PUBLICATIONS

International Search Report for Application No. PCT/CN2015/080893 dated Sep. 14, 2015.

(Continued)

*Primary Examiner* — Golam M Shameem
(74) *Attorney, Agent, or Firm* — Lerner, David, Littenberg, Krumholz & Mentlik, LLP

(57) ABSTRACT

Disclosed is a new method for preparing an azetidinone compound represented by formula (I). The carboxylic ketoester represented by formula (II) serves as the raw material and is subjected to Grignard addition, stereoselective dehydration, ester group reduction, hydroxyl group protection, addition with imine after condensation with a chiral auxiliary, cyclization and deprotection to obtain the compound represented by formula (I). The present invention has advantages of easily available raw material, a few synthetic steps, simple operation, high yield, good stereoselectivity and low cost, and can be used for industrial production.

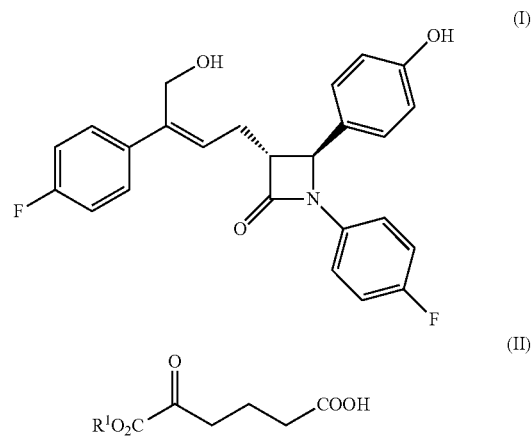

8 Claims, No Drawings

(56) References Cited

U.S. PATENT DOCUMENTS 5,925,631 A * 7/1999 Black .................... C07C 311/29
514/183
8,623,855 B2 1/2014 Bai et al.
2015/0218091 A1 8/2015 Wei et al.

FOREIGN PATENT DOCUMENTS

WO 2014036956 A1 3/2014
WO 2014131371 A1 9/2014

OTHER PUBLICATIONS

Mani et al., "Stereoselective Synthesis of Z-a-Aryl-a,b-unsaturated Esters," J. Org. Chem., vol. 71, No. 13, pp. 5039-5042, 2006.
Cossy et al., "Oxidative Cleavage of 2-Substituted Cycloalkane-1,3-diones and of Cyclic β-Ketoesters by Copper Perchlorate/Oxygen," Tetrahedron Letters, vol. 35, No. 33, pp. 6089-6092, 1994.

* cited by examiner

METHOD FOR PREPARING AZETIDINONE COMPOUND AND INTERMEDIATE OF AZETIDINONE COMPOUND

CROSS REFERENCE TO RELATED APPLICATIONS

The present application is a national phase entry under 35 U.S.C. § 371 of International Application No. PCT/CN2015/080893, filed Jun. 5, 2015, which claims priority from Chinese Patent Application No. 201410251262.5, filed Jun. 9, 2014, all of which are hereby incorporated herein by reference.

TECHNICAL FIELD

The present invention relates to the field of chemistry, especially to a new preparation method of a cholesterol absorption inhibiting agent, the compound of formula (I), i.e. (3R,4S)-4-(4-hydroxyphenyl)-3-[3-(4-fluorophenyl)-4-hydroxybut-2(Z)-enyl]-1-(4-fluorophenyl)azetidin-2-one and the synthesized intermediate thereof.

TECHNICAL BACKGROUND

In western countries, coronary atherosclerotic heart disease (coronary heart disease) is the leading cause of death, and cholesterol is one of the risk factors that cause this disease. At present, there are two kinds of medicines that are used to the reduction of plasma cholesterol levels. One is Statins, which is a HMG-CoA reductase inhibitor, and can effectively inhibit the biosynthesis of cholesterol in vivo. Another kind of role is to prevent the absorption of cholesterol from small intestine, and Ezetimibe is a common cholesterol absorption inhibitor. U.S. Pat. No. 5,846,966 describes Ezetimibe, the chemical structure is as follows:

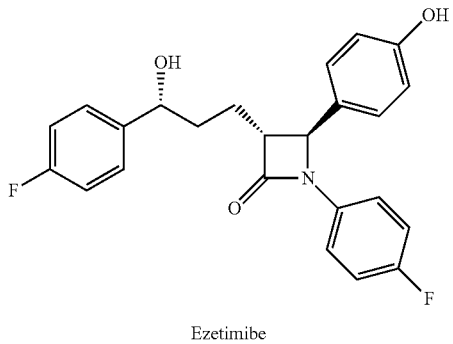 [SMILES: O=C1[C@H](CC[C@@H](O)c2ccc(F)cc2)[C@@H](c2ccc(O)cc2)N1c1ccc(F)cc1]

Ezetimibe

The side chain at the 3-position carbon of the azetidinone is a chiral benzyl alcohol, and the chiral carbon is of S configuration. The structure-activity relationship shows that the pharmacodynamic properties of S configuration is better than the R configuration, which indicates that the stereochemistry of the carbon of the benzyl is very important.

WO2011/017907 discloses a new kind of azetidinone compounds, which can also effectively inhibit the absorption of cholesterol, but the side chain on the 3-carbon of the azetidinone is not a chiral benzyl alcohol but an achiral allyl alcohol, and the pharmacodynamic properties of the double bonds of Z configuration is much better than the double bonds of E configuration. Among this kind of compounds, the chemical structure of the compound with the best pharmacodynamic properties, i.e. (3R,4S)-4-(4-hydroxyphenyl)-3-[3-(4-fluorophenyl)-4-hydroxybut-2(Z)-enyl]-1-(4-fluorophenyl)azetidin-2-one is as follows:

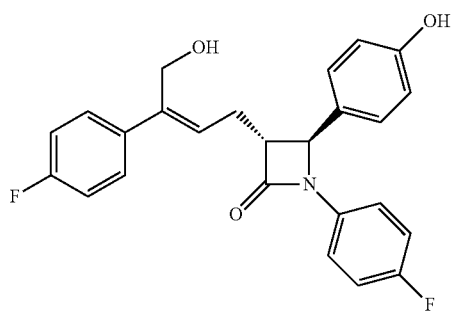 [SMILES: O=C1[C@H](C/C=C(\CO)c2ccc(F)cc2)[C@@H](c2ccc(O)cc2)N1c1ccc(F)cc1]

Because the synthetic route for the preparation of the new azetidinone compounds mentioned in WO2011/017907 is too long, and double bonds of Z configuration cannot be produced stereoselectively, some of the steps are not suitable for industrial production, therefore, it is necessary to develop a new process route. The present invention provides a new method for preparing this kind of azetidinone. The raw materials of the new process are easily obtained, and the process has a few synthetic steps, the double bond of Z configuration can be produced stereoselectively, and the operation is simple, the yield is high, the cost is low, and the process can be used for industrial production.

SUMMARY OF THE INVENTION

One of the objects of the present invention is to provide new key intermediates (the compounds of formula III, IV and V) for the preparation of the compound of formula (I) and the preparation methods thereof:

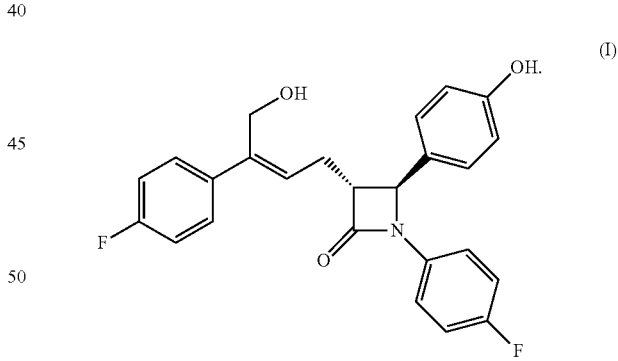

From one aspect of the present invention, new intermediates of formula III, IV and V that can be used to prepare the compound of formula (I) are provided:

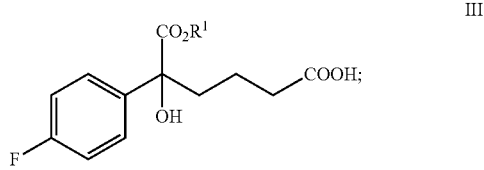

-continued

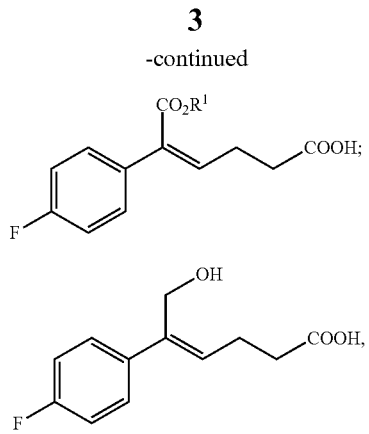

IV

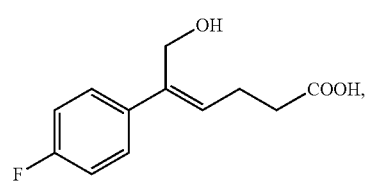

V wherein, $R^1$ is $C_1$-$C_6$ alkyl, preferably methyl, ethyl or isopropyl, more preferably methyl.

From another aspect of the present invention, a method for preparing the compound of formula III is provided, said method comprising:
carrying out a Grignard addition selectively to the ketone of formula II with 4-fluorophenyl magnesium halide which is used as a Grignard reagent to obtain the tertiary alcohol of formula III:

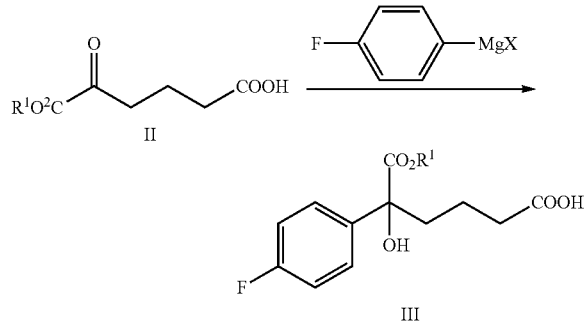

wherein, $R^1$ is $C_1$-$C_6$ alkyl, preferably methyl, ethyl or isopropyl, more preferably methyl; X is a halogen, preferably chlorine, bromine or iodine.

4-fluorophenyl magnesium halide is preferably 4-fluorophenyl magnesium bromide.

The molar ratio of the compound of formula II to 4-fluorophenyl magnesium halide in the reaction is 1:1.0~5.0, preferably 1:1.1~3.0.

The temperature of the reaction is controlled between −78° C.~5° C., preferably −50° C.~10° C.

From another aspect of the present invention, a method for preparing the compound of formula IV is provided, the method comprising the following step: under the action of a dehydrating agent, the tertiary alcohol of formula III is dehydrated stereoselectively to obtain the (Z)-α,β-unsaturated ester of formula IV:

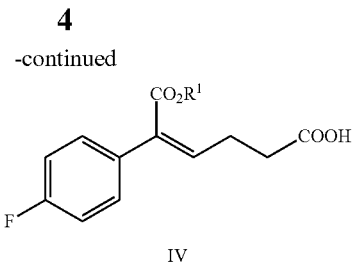

wherein, $R^1$ is $C_1$-$C_6$ alkyl, preferably methyl, ethyl or isopropyl, more preferably methyl. In the reaction, the dehydrating agent is selected from concentrated sulfuric acid, p-toluenesulfonic acid, phosphoric acid, triflic anhydride or methanesulfonic acid, preferably triflic anhydride.

In the reaction, the molar ratio of the compound of formula III to the dehydrating agent is 1:1.0~3.0, preferably 1:1.0~1.5.

The solvent of the reaction is selected from dichloromethane or toluene, preferably dichloromethane.

From another aspect of the invention, a method for preparing the compound of formula V is provided, the method comprising: selectively reducing the ester of formula IV to the alcohol of formula V under the action of a reducing agent:

wherein, $R^1$ is $C_1$-$C_6$ alkyl, preferably methyl, ethyl or isopropyl, more preferably methyl. The reducing agent of the reaction is preferably diisobutylaluminium hydride (DIBAH).

The solvent of the reaction is selected from dichloromethane, tetrahydrofuran, toluene or dioxane, preferably toluene.

The molar ratio of the compound of formula IV to the reducing agent is 1:2.5~5.0, preferably 1:3.0~4.0.

Another object of the present invention is to provide a new method for preparing the compound of formula (I) according to the above intermediates, to further provide an improved and simple method for preparing compound of formula (I) with good selectivity and high yield.

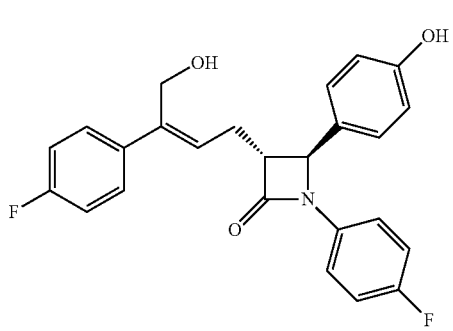

That is to say, a method for preparing the compound (3R,4S)-4-(4-hydroxyphenyl)-3-[3-(4-fluorophenyl)-4-hydroxybut-2(Z)-enyl]-1-(4-fluorophenyl)azetidin-2-one, wherein the compound of formula (I) is a new azetidinone compound that can reduce blood cholesterol.

The method comprising the following steps:

(1) Carrying out a Grignard addition selectively to the ketone of formula II with 4-fluorophenyl magnesium halide which is used as a Grignard reagent to obtain the tertiary alcohol of formula III:

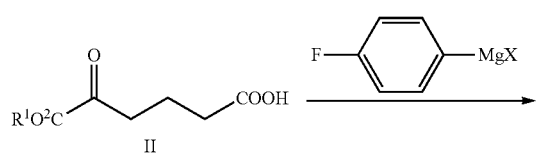

wherein, $R^1$ is $C_1$-$C_6$ alkyl, preferably methyl, ethyl or isopropyl, more preferably methyl; X is a halogen, preferably chlorine, bromine or iodine.

(2) Under the action of a dehydrating agent, the tertiary alcohol of formula III is dehydrated stereoselectively to obtain the (Z)-α,β-unsaturated ester of formula IV:

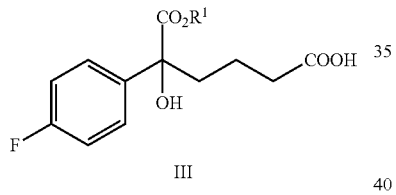

(3) Under the action of a reducing agent, the ester of formula IV is reduced selectively to the alcohol of formula V:

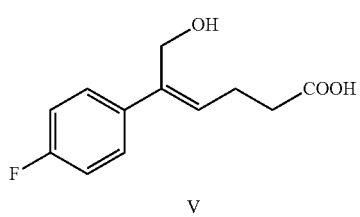

(4) Reacting the compound of formula V with a hydroxyl protectant to obtain the compound of formula VI:

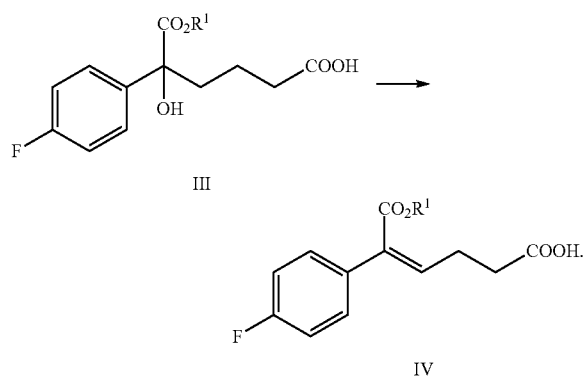

wherein $R^2$ is an alcoholic hydroxyl protecting group, such as: acetyl, substituted or unsubstituted benzoyl (the "substituted" comprises halogen, alkyl, nitro substituted) etc.

(5) Converting the carboxylic acid of formula VI into mixed anhydride or acyl halide, then reacting with (S)-4-phenyl-2-oxazolidone of formula VII which is used as a chiral auxiliary to obtain a derivative of oxazolidone of formula VIII:

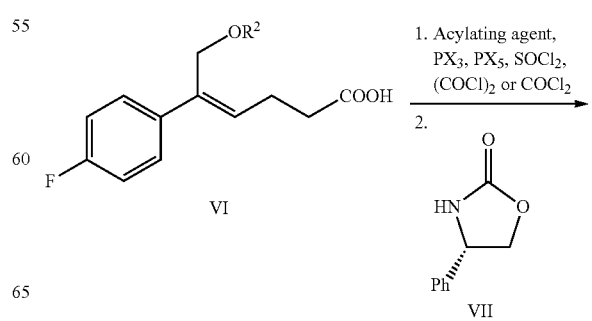

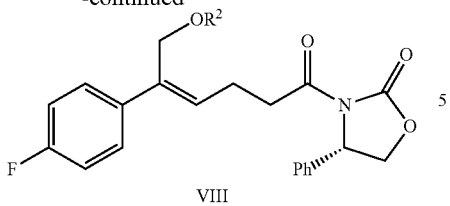

VIII

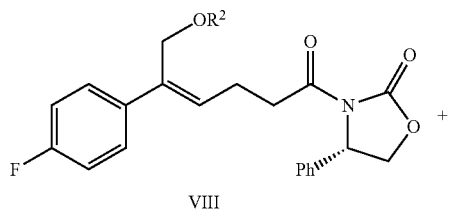

VIII + wherein the carboxylic acid of formula VI is reacted with an acylating agent to produce mixed anhydride; or the carboxylic acid of formula VI is reacted with phosphorus trihalide, phosphorus pentahalide, dichlorosulfane (SOCl$_2$), oxalyl chloride((COCl)$_2$) or phosgene (COCl$_2$) to produce acyl halide; X is chlorine or bromine.

In addition, step (4) and step (5) can be combined i.e. the compound of formula VIII can be prepared from the compound of formula V through a one-pot method, the method comprises the following steps: protecting the alcoholic hydroxyl of formula V in a suitable solvent to obtain the compound of formula VI, further converting the carboxylic acid of formula VI into mixed anhydride or acyl halide without separation and purification, then reacting with (S)-4-phenyl-2-oxazolidone of formula VII which is used as a chiral auxiliary to obtain a derivative of oxazolidone of formula VIII:

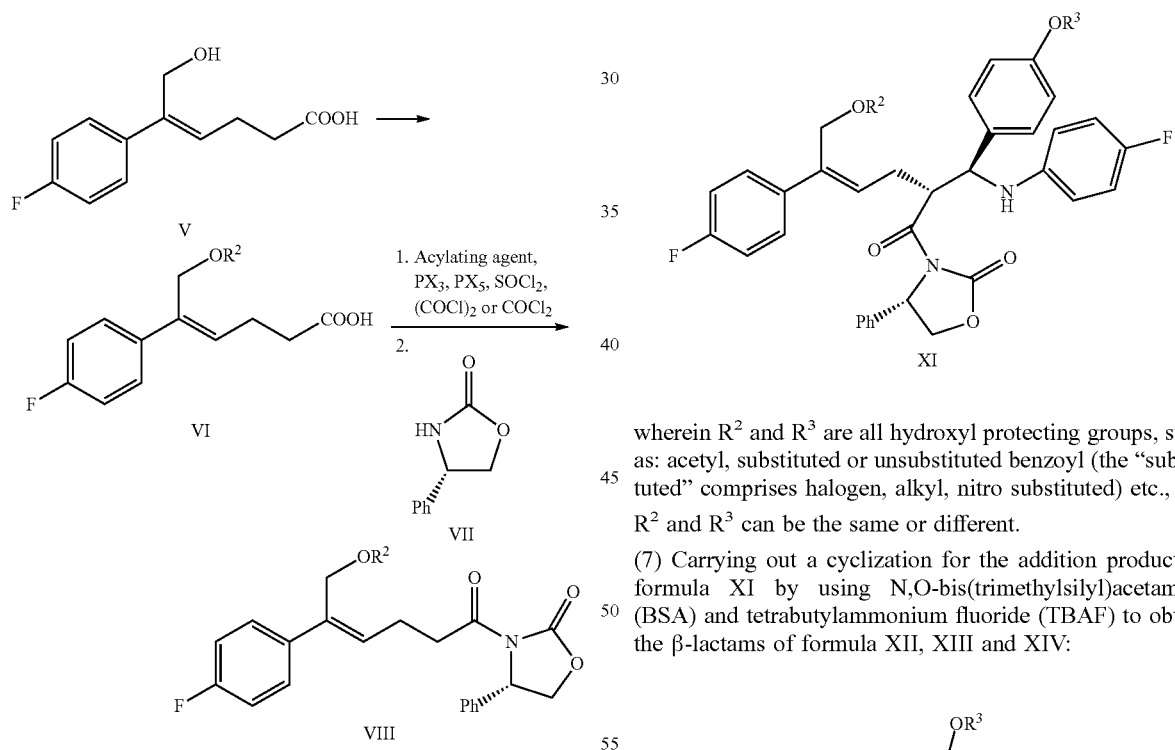

wherein the carboxylic acid of formula VI is reacted with an acylating agent to produce mixed anhydride; or the carboxylic acid of formula VI is reacted with phosphorus trihalide, phosphorus pentahalide, dichlorosulfane (SOCl$_2$), oxalyl chloride((COCl)$_2$) or phosgene (COCl$_2$) to produce acyl halide; X is chlorine or bromine.

(6) Under the presence of Lewis acids (titanium tetrachloride (TiCl$_4$) and tetraisopropyl titanate) and tertiary amine, reacting the derivative of oxazolidone of formula VIII with the imine of formula IX to obtain an addition product of formula XI:

IX

XI wherein R$^2$ and R$^3$ are all hydroxyl protecting groups, such as: acetyl, substituted or unsubstituted benzoyl (the "substituted" comprises halogen, alkyl, nitro substituted) etc., R$^2$ and R$^3$ can be the same or different.

(7) Carrying out a cyclization for the addition product of formula XI by using N,O-bis(trimethylsilyl)acetamide (BSA) and tetrabutylammonium fluoride (TBAF) to obtain the β-lactams of formula XII, XIII and XIV:

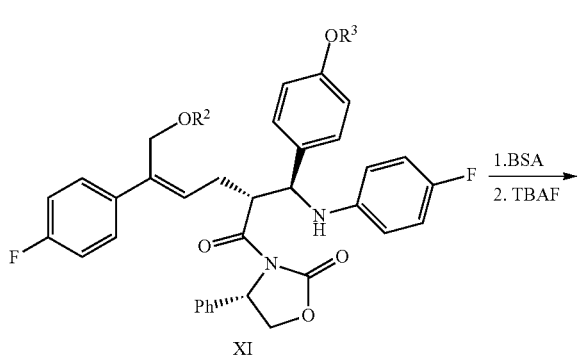

XI

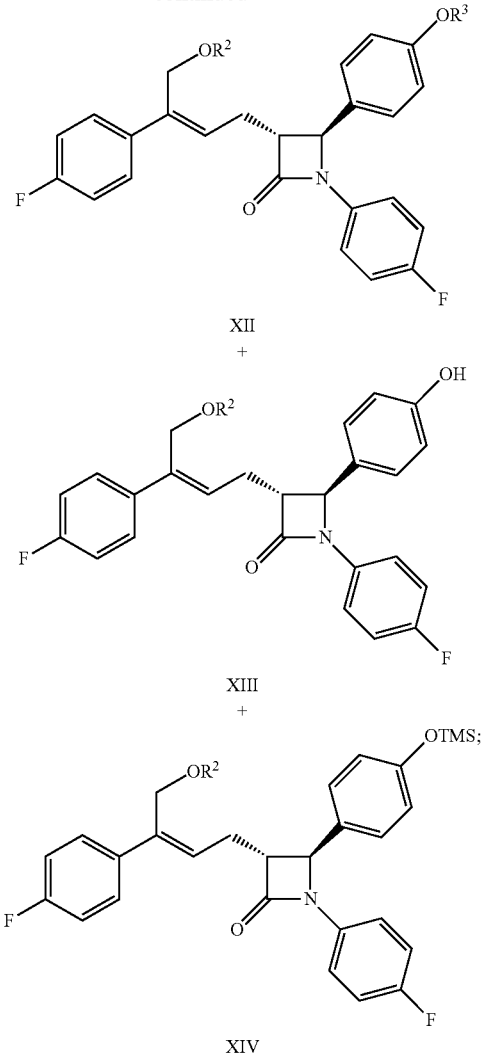

XII
+

XIII
+

XIV (8) Obtaining the compound of formula (I) via the deprotection of the mixture of the compounds of formula XII, XIII and XIV in step (7) under the action of alkali:

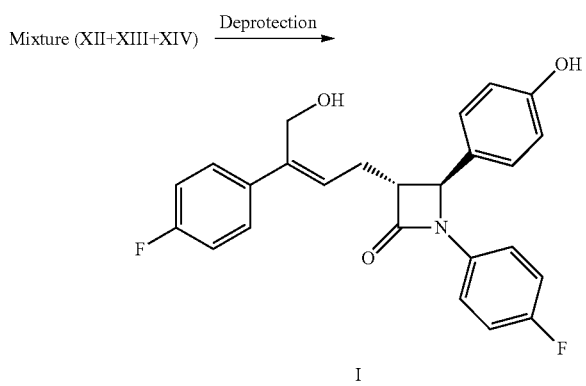

In the above reaction steps, wherein, $R^1$ is $C_1$-$C_6$ alkyl, preferably methyl, ethyl or isopropyl, more preferably methyl; $R^2$ and $R^3$ are all hydroxyl protecting groups, such as: acetyl, substituted or unsubstituted benzoyl (the "substituted" comprises halogen, alkyl, nitro substituted) etc., $R^2$ and $R^3$ can be the same or different.

In step (1), the molar ratio of the compound of formula II to 4-fluorophenyl magnesium halide is 1:1.0~5.0, preferably 1:1.1~3.0; 4-fluorophenyl magnesium halide is preferably 4-fluorophenyl magnesium bromide. The reaction temperature is controlled between −78° C.~−5° C., preferably −50° C.~−10° C.

In step (2), the dehydrating agent is selected from concentrated sulfuric acid, p-toluenesulfonic acid, phosphoric acid, triflic anhydride or methanesulfonic acid, preferably triflic anhydride. The molar ratio of the compound of formula III to the dehydrating agent is 1:1.0~3.0, preferably 1:1.0~1.5. The solvent of the reaction is selected from dichloromethane or toluene, preferably dichloromethane.

In step (3), the molar ratio of the compound of formula IV to the reducing agent is 1:2.5~5.0, preferably 1:3.0~4.0. The reducing agent is preferably diisobutylaluminium hydride (DIBAH). The solvent of the reaction is selected from dichloromethane, tetrahydrofuran, toluene or dioxane, preferably toluene.

In step (4), the alcoholic hydroxyl protecting group $R^2$ is preferably substituted or unsubstituted benzoyl, more preferably substituted benzoyl, wherein the "substituted" is preferably substituted by nitro, more preferably substituted by nitro at the 3-position. The solvent of the reaction is selected from N,N-dimethylformamide (DMF), N,N-dimethylacetamide (DMA), dimethylsulfoxide (DMSO), 1,3-dimethylpropyleneurea (DMPU) or hexamethylphosphoramide (HMPA), preferably N,N-dimethylacetamide (DMA). The molar ratio of the compound V to the hydroxyl protecting agent is 1:1.0~3.0, preferably 1:1.2~2.3.

In step (5), the acylating agent is selected from pivaloyl chloride, 3-nitrobenzoyl chloride or isobutyl chloroformate, preferably pivaloyl chloride or 3-nitrobenzoyl chloride. The molar ratio of the compound of formula VI to the acylating agent is 1:1.0~2.0, preferably 1:1.1~1.6. The molar ratio of the compound of formula VI to (S)-4-phenyl-2-oxazolidone of formula VII is 1:0.5~1.5, preferably 1:0.8~1.1.

When the step (4) is combined with the step (5), i.e., the compound of formula VIII is prepared from the compound of formula V through a one-pot method, the alcoholic hydroxyl protecting group $R^2$ is preferably substituted or unsubstituted benzoyl, more preferably substituted benzoyl, wherein the "substituted" is preferably substituted by nitro, more preferably substituted by nitro at the 3-position. The solvent is selected from N,N-dimethyl formamide (DMF), N,N-dimethylacetamide (DMA), dimethylsulfoxide (DMSO), 1,3-dimethylpropyleneurea (DMPU) or hexamethylphosphoramide (HMPA), preferably N,N-dimethylacetamide (DMA). The molar ratio of the compound V to the alcoholic hydroxyl protecting agent is 1:1.0~3.0, preferably 1:1.0~1.5. The acylating agent is selected from pivaloyl chloride, 3-nitrobenzoyl chloride or isobutyl chloroformate, preferably pivaloyl chloride or 3-nitrobenzoyl chloride. The molar ratio of the compound of formula V to the acylating agent is 1:1.0~2.0, preferably 1:1.0~1.5. The molar ratio of the compound of formula V to (S)-4-phenyl-2-oxazolidone is 1:0.5~1.5, preferably 1:0.7~1.1.

In step (6), the phenolic hydroxyl protecting group $R^3$ is preferably substituted or unsubstituted benzoyl, more preferably substituted benzoyl, wherein the "substituted" is preferably substituted by nitro, more preferably substituted by nitro at the 3-position. The tertiary amine is preferably diisopropylethylamine (DIPEA). The molar ratio of the compound of formula VIII to the imine (the compound of formula IX) is 1:1.0~2.0, preferably 1:1.0~1.2; wherein the reaction temperature is controlled between −90° C.~0° C., preferably −80° C.~−20° C.; wherein alcohols, acids or mixed liquids of acids diluted by organic solvents can be used in the post-processing quenching reaction; wherein the alcohols are selected from methanol, ethanol, propanol, isopropanol, tertiary butanol, preferably isopropanol; wherein the acids are selected from inorganic acids and organic acids, comprising hydrochloric acid, sulfuric acid, nitric acid, hydrobromic acid, formic acid, acetic acid, trifluoroacetic acid, methanesulfonic acid, trifluoromethanesulfonic acid, benzoic acid, benzenesulfonic acid, p-toluenesulfonic acid, citric acid, maleic acid or tartaric acid, preferably organic acids, comprising formic acid, acetic acid, trifluoroacetic acid, methanesulfonic acid, trifluoromethanesulfonic acid, benzoic acid, benzenesulfonic acid, p-toluenesulfonic acid, citric acid, maleic acid or tartaric acid, more preferably acetic acid or trifluoroacetic acid.

In step (7), the solvent of the reaction is selected from acetonitrile or toluene, preferably toluene. The molar ratio of the compound of formula XI to N,O-bis(trimethylsilyl) acetamide (BSA) is 1:1.0~5.0, preferably 1:2.0~4.0; and the molar ratio of the compound of formula XI to tetrabutylammonium fluoride trihydrate (TBAF) is 1:0.1~0.5, preferably 1:0.1~0.3.

In step (8), the solvent used for the deprotection of the compounds of formula XII, XIII and XIV is preferably acetone, the alkali is preferably aqueous lithium hydroxide. The molar ratio of the alkali to the compound XI in step (7) is 3.0~5.0:1.

In another aspect, the present invention also relates to the protection of the intermediates of formula III, IV and V.

Some of the terms used in the present invention are defined as follows:

The "halogen" refers to fluorine, chlorine, bromine and iodine.

The "alkyl", when it is a group or a part of a group, it refers to a linear or branched aliphatic hydrocarbon group. Most preferably, it is a $C_1$~$C_6$ alkyl, unless otherwise stated, the examples of a linear or branched $C_1$~$C_6$ alkyl comprising, but is not limited to: methyl, ethyl, n-propyl, 2-propyl, n-butyl, isobutyl, tertiary butyl, hexyl and so on.

The "room temperature" refers to 20~30° C.

The preferred reaction conditions of the present invention are listed in the following schemes:

Step (1):

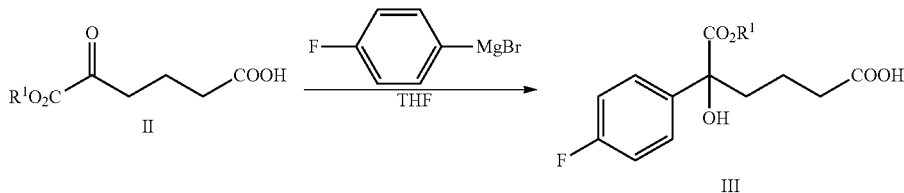

Step (2):

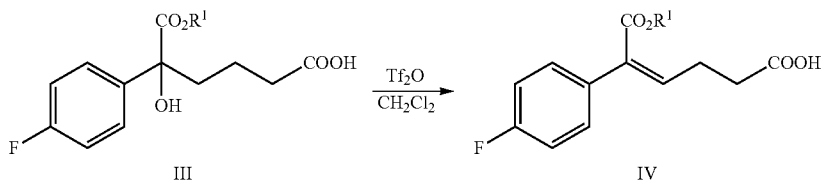

Step (3):

Step (4):

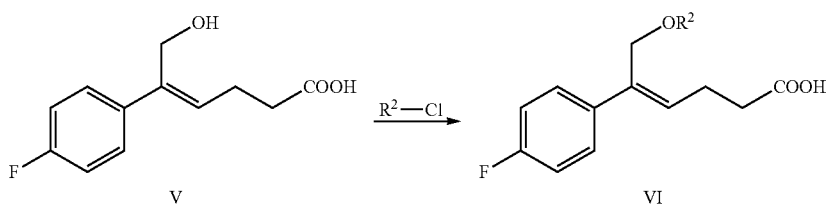

Step (5):
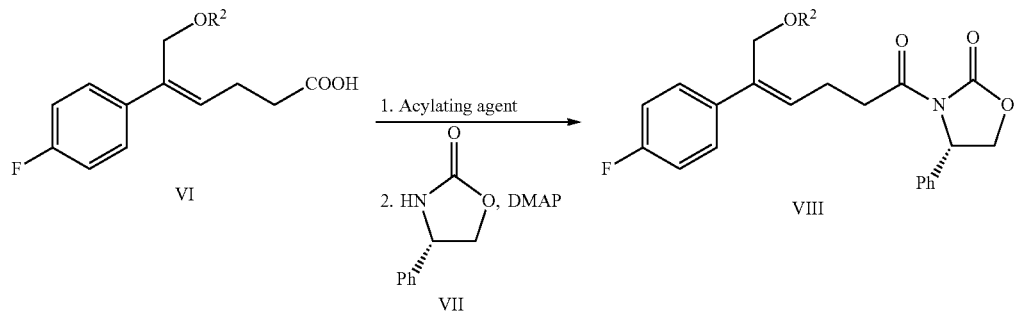
Step (6):
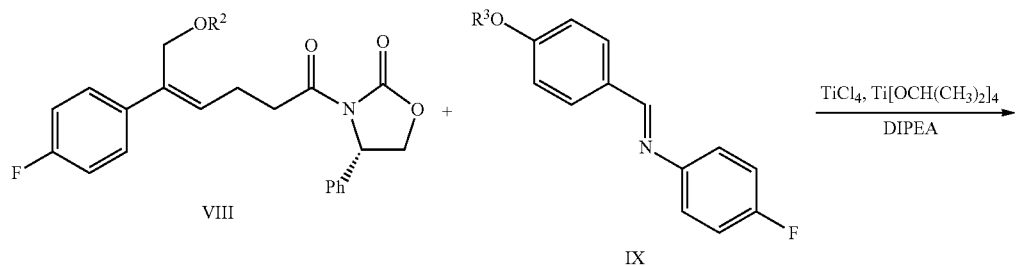
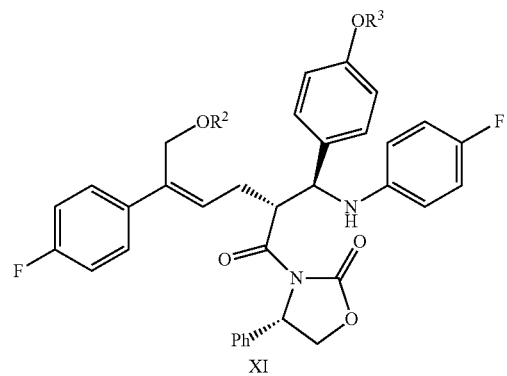
Step (7):
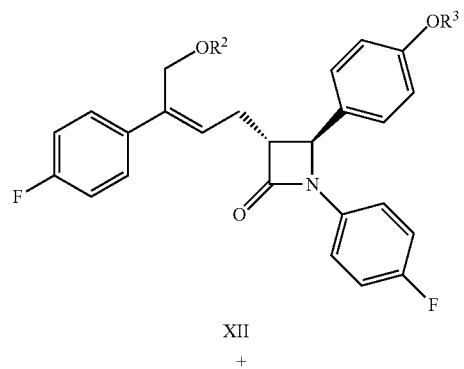

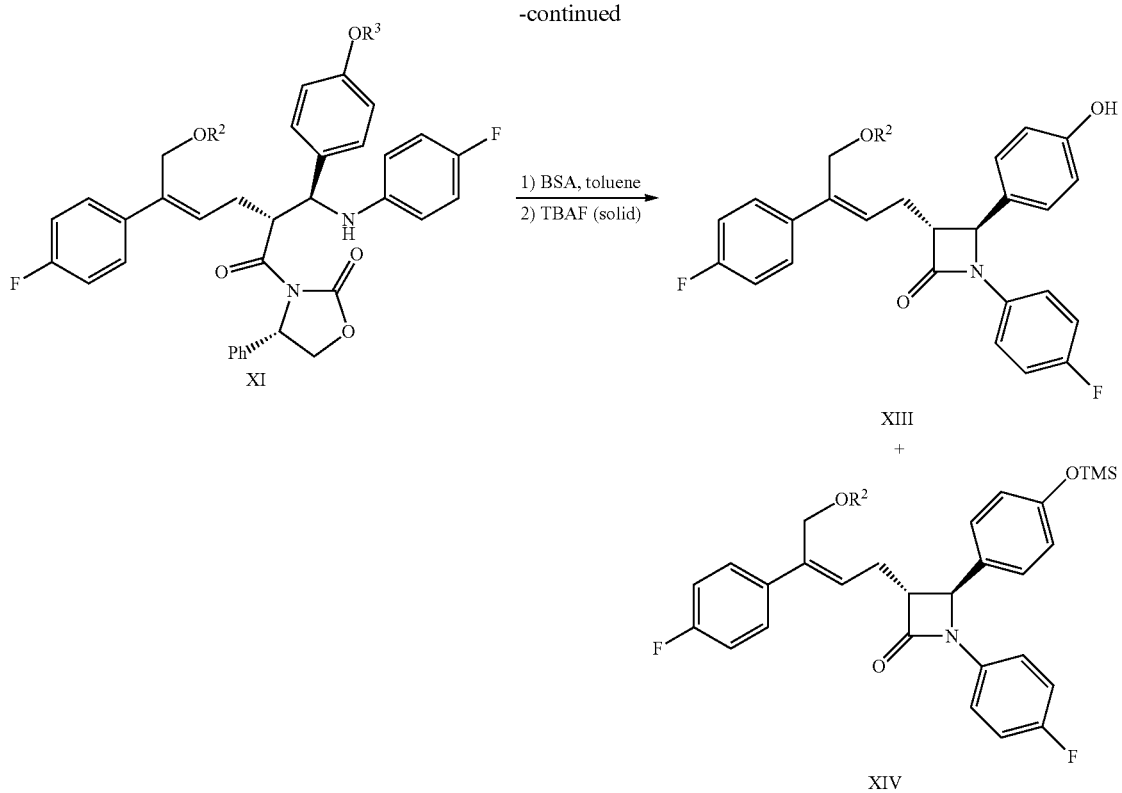

Step (8):

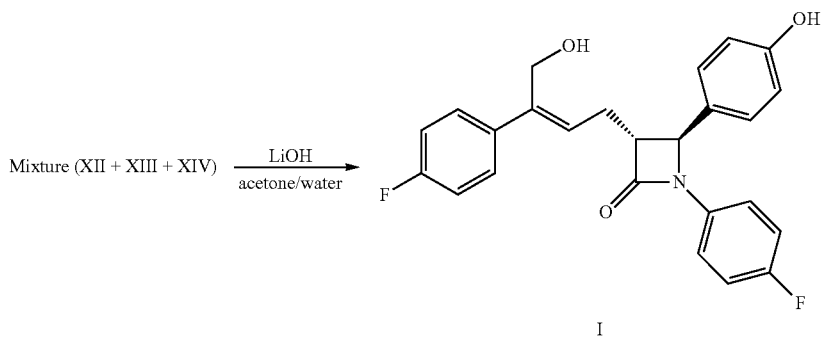

In the above reaction schemes, Tf$_2$O is triflic anhydride, DIBAH is diisobutylaluminium hydride, DMAP is 4-dimethylamino-pyridine, DIPEA is diisopropylethylamine, BSA is N,O-bis(trimethylsilyl)acetamide, and TBAF is tetrabutylammonium fluoride, wherein R$^1$ is C$_1$-C$_6$ alkyl, preferably methyl, ethyl or isopropyl, more preferably methyl; R$^2$ and R$^3$ are all hydroxyl protecting groups, such as: acetyl, substituted or unsubstituted benzoyl (the "substituted" comprises halogen, alkyl, nitro substituted) etc., R$^2$ and R$^3$ can be the same or different.

DETAILED DESCRIPTION OF THE PRESENT APPLICATION

The preparation method will be further illustrated with the combination of the above reaction steps (1)~(8) below.

In step (1), the alcohol of formula III is produced via the addition of the keto-carbonyl of formula II and a Grignard reagent. The reaction process is as follows: the compound of formula II (1 equivalent) is added into an anhydrous solvent (such as tetrahydrofuran or diethyl ether, preferably tetrahydrofuran), the temperature is decreased to between −78° C.~−5° C. (preferably −50° C.~−10° C.), 1.0~5.0 equivalents (preferably 1.1~3.0 equivalents) Grignard reagent (such as 4-fluorophenyl magnesium halide, preferably 4-fluorophenyl magnesium bromide) is added, then the temperature is kept for the reaction for 1~2 hours under stirring, the reaction is terminated by aqueous ammonium chloride. The product, the compound of formula III is separated via extraction and is purified via crystallization.

In the reaction, the raw material, carboxylic ketoester (the compound of formula II) can be obtained via the synthesis method in the document, *Tetrahedron Letters*, 1994, 35, 6089-6092, i.e. in the acetonitrile solvent, the ketone of formula II is obtained via the oxidation and ring-opening of cyclopentanone-2-carboxylate under the catalyzation of cupric salt (such as CuCl$_2$.2H$_2$O, CuSO$_4$.5H$_2$O, Cu(OAc)$_2$.H$_2$O or Cu(ClO$_4$)$_2$. 6H$_2$O). The equation is as follows:

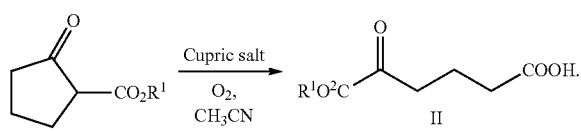

In step (2), the (Z)-α,β-unsaturated ester of formula IV is produced via the stereoselective dehydration of the tertiary alcohol of formula III. It is reported in *J. Org. Chem.* 2006, 71, 5039-5042 that (Z)-α-aryl-α,β-unsaturated ester is obtained via selective dehydration of α-aryl-α-hydroxyl ester under the action of dehydrating agent (triflic anhydride) and alkali (such as pyridine or DMAP). The reaction time reported in the literature is long (the reaction lasts 10~12 hours at room temperature), and it is not reported whether ω-carbonyl-α-aryl-α-hydroxyl ester is suitable for the reaction. The reaction of the prior art is improved by the method of the present invention to increase the efficiency and selectivity of producing (Z)-ω-carbonyl-α-aryl-α,β-unsaturated ester. After the improvement, the reaction time is shortened, the selectivity is improved and alkali (pyridine or DMAP) catalyzation is no longer needed. Carboxylic acid hydroxyl ester (the compound of formula III, 1 equivalent) is dissolved in a non-polar anhydrous solvent (such as dichloromethane), 1.0~3.0 equivalents (preferably 1.0~1.5 equivalents) dehydrating agent (preferably triflic anhydride) is added at 5° C.~15° C., the reaction was refluxed for 1~2 hours and then is terminated by water. The product, the compound of formula IV is separated via extraction.

In step (3), the ester group of the compound of formula IV is reduced selectively and the carbonyl group is retained. The compound of formula IV (1 equivalent) is dissolved in a suitable solvent (preferably toluene), alkali (such as triethylamine or diisopropylethylamine) is added at room temperature to allow the carbonyl group to form a salt, then the temperature is decreased, 2.5~5.0 equivalents (preferably 3.0~4.0 equivalents) reducing agent (preferably diisobutylaluminium hydride) is added slowly at the temperature of –30° C.~–5° C., the reaction is stirred for 20~60 minutes. After completion of the reaction, the reaction solution is added slowly to alkali (such as aqueous potassium hydroxide, lithium hydroxide or sodium hydroxide, preferably aqueous sodium hydroxide) at the temperature of t<15° C., stirred, layered, the water phase is extracted by a suitable solvent (such as dichloromethane) to remove organic impurities, then is acidified by an acid (such as hydrochloric acid), then it is extracted by a suitable solvent (such as ethyl acetate), the product is separated and purified via crystallization to obtain (Z)-5-(4-fluorophenyl)-6-hydroxyl-hex-4-enoic acid (the compound of formula V).

In step (4), the hydroxyl group of the compound of formula V is protected selectively and the carbonyl group is retained. The compound of formula V (1 equivalent) is dissolved in a suitable anhydrous solvent (preferably N,N-dimethylacetamide), 1.0~3.0 equivalents (preferably 1.2~2.3 equivalents) hydroxyl protecting agent (preferably nitrobenzoyl chloride, more preferably 3-nitrobenzoyl chloride) is added at –5° C.~40° C. and reacted for 5~6 hours. Suitable alkali (such as pyridine) is added to hydrolyze the resulting mixed anhydride, then alkali (such as imidazole) is added to remove the carboxylic acid of the protecting agent liberated from hydrolysis by forming a salt. The product, the compound of formula VI is separated via extraction.

In step (5), the compound of formula VI (1 equivalent) is dissolved in an anhydrous inert solvent (such as tetrahydrofuran or dichloromethane, preferably dichloromethane), 1.0~2.0 equivalents (preferably 1.1~1.6 equivalents) acylating agent (such as pivaloyl chloride, isobutyl chloroformate or 3-nitrobenzoyl chloride, preferably pivaloyl chloride or 3-nitrobenzoyl chloride) is added, at the same time, the mixture is reacted for 3~4 hours at room temperature in the presence of alkali (such as triethylamine) to obtain the mixed anhydride. Then 0.5~1.5 equivalents (preferably 0.8~1.1 equivalents) (S)-4-phenyl-2-oxazolidone of formula VII is added to the obtained mixed anhydride solution, 0.1~0.3 equivalent suitable catalyst (such as 4-dimethylaminopyridine) is added and stirred for 3~5 hours at room temperature to form an acylated derivative of oxazolidone of formula VIII via condensation. The product is separated via extraction and is purified via crystallization.

In addition, step (4) can be combined with step (5), the compound of formula VIII can be produced from the compound of formula V through an one-pot method. The compound of formula V (1 equivalent) is dissolved in a suitable anhydrous solvent (preferably N,N-dimethylacetamide), 1.0~3.0 equivalents (preferably 1.0~1.5 equivalents) hydroxyl protecting agent (preferably nitrobenzoyl chloride, preferably 3-nitrobenzoyl chloride) is added at –5° C.~40° C., after the completion of the reaction, the reaction solution is added to the solution of 1.0~2.0 equivalents (preferably 1.0~1.5 equivalents) acylating agent (such as pivaloyl chloride, isobutyl chloroformate or 3-nitrobenzoyl chloride, preferably pivaloyl chloride or 3-nitrobenzoyl chloride, more preferably 3-nitrobenzoyl chloride) and alkali (such as triethylamine) dissolved in the anhydrous inert solvent (such as tetrahydrofuran or dichloromethane, preferably dichloromethane), then 0.5~1.5 equivalents (preferably 0.7~1.1 equivalents) chiral auxiliary ((S)-4-phenyl-2-oxazolidone) of formula VII and 0.1~0.5 equivalent suitable catalyst (such as 4-dimethylamino-pyridine) are added, the temperature was kept for the reaction for 6~7 hours, the acylated derivative of oxazolidone of formula VIII is produced via condensation. The product is separated via extraction and is purified via crystallization.

In step (6), the temperature is decreased at the presence of a suitable anhydrous solvent (such as anhydrous dichloromethane) and the protection of a dry inert gas flow (such as nitrogen), Lewis acids $TiCl_4$ (1.1~1.5 equivalents) and tetraisopropyl titanate (0.3~0.5 equivalent) are added at the temperature of –5° C.~0° C. to react under stirring for 20~40 minutes to produce titanium reagent, which is retained to be used. The acylated derivative of oxazolidone of formula VIII (1 equivalent), the protected imine compound of formula IX (1.0~2.0 equivalents, preferably 1.0~1.2 equivalents) are dissolved in anhydrous solvent (such as anhydrous dichloromethane), tertiary amine (such as diisopropylethylamine) is added, stirred for 10 minutes, the temperature is decreased, the titanium reagent produced above is added slowly drop by drop at the temperature of –90° C.~0° C. (preferably –80° C.~–20° C.), the temperature was kept for the reaction continuously, after the completion of the reaction, a suitable amount of acid (preferably acetic acid or trifluoroacetic acid) is added to quench the reaction. Meanwhile, the titanium salt is removed by adding dilute sulphuric acid, then the compound of formula XI is separated via extraction and purified via crystallization.

In step (7), the compound of formula XI (1 equivalent) is dissolved in a suitable solvent (such as toluene), 1.0~5.0 equivalents (preferably 2.0~4.0 equivalents) N,O-bis(trimethylsilyl)acetamide (BSA) is added, and reacted for 2~3 hours at the temperature of 50° C.~70° C., then 0.1~0.5 equivalent (preferably 0.1~0.3 equivalent) tetrabutylammonium fluoride (TBAF) is added, reacted for 2~5 hours at the temperature, the mixture of the compounds of formula XII, XIII and XIV are produced via cyclization.

In step (8), the mixture of the compounds of formula XII, XIII and XIV is dissolved in a suitable solvent (preferably acetone), 3~5 equivalents (it is calculated based on that the feed amount of the compound XI in step 7 as 1 equivalent) alikali (preferably aqueous lithium hydroxide) is added at room temperature to hydrolyze the hydroxyl protecting group, the mixture is reacted under stirring for 2~3 hours, then acidified with a weak acid (such as diluted sulphuric acid or diluted hydrochloric acid), extracted, concentrated and separated via column chromatography to obtain the compound of formula I, which is purified via recrystallization.

In the present invention, the carboxylic ketoester represented by formula (II) is used as the raw material and is subjected to Grignard addition, stereoselective dehydration, ester group reduction, hydroxyl group protection, addition with imine after condensation with a chiral auxiliary, cyclization and deprotection to obtain the compound represented by formula (I). The advantages of the present invention can be summarized as follows:

a) Compared with the preparation method reported in WO 2011/017907, the number of synthetic steps are significantly decreased, from 14 steps to 8 steps; at the same time, the column chromatography is replaced by multiple times of recrystallization to simplify the purification operation and decrease the cost.

b) In step 2 of the present method, the Z alkene is obtained via stereoselection, allowing the subsequent multistep reactions to start with a single isomer, which simplify the separation operation and decrease the cost.

c) In order to protect the hydroxyl groups (including alcoholic hydroxyl groups and phenolic hydroxyl groups), nitro substituted benzoyl is used, preferably the benzoyl with nitro substituted at 3-position is used. From one aspect, the ability of crystallization of the key intermediate is enhanced so that it can be purified effectively in a simple crystallization operation; from another aspect, it is advantageous for the deprotection under mild environment subsequently and prevent the occurrence of the accompanied side reactions (such as the open of the β-lactam ring) under alkaline condition.

d) The method of the present invention is suitable for industrialized production and the yield is high.

In summary, the present invention has advantages of easily available raw materials, a few synthetic steps, simple operation, high yield, good stereoselectivity and low cost, and can be used for industrial production.

EMBODIMENTS

The following examples are solely for the illustration of the present invention, the present invention is not limited by those examples.

Example 1

Preparation of Raw Material Imine IXa

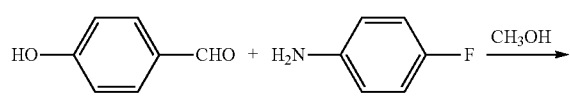

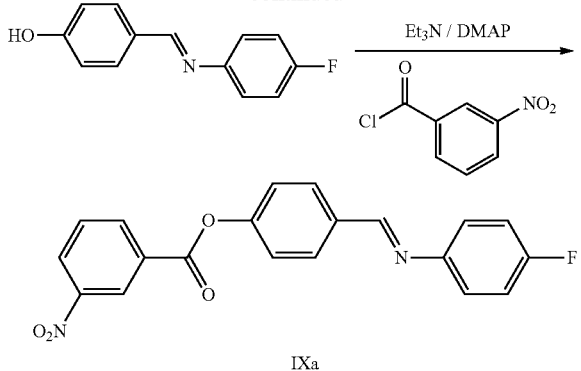

Step 1: 12 Kg 4-hydroxybenzaldehyde and 60 L methanol were added to a 100 L reaction tank and were dissolved under stirring, 12 Kg 4-fluoroaniline was added drop by drop at room temperature, the mixture was reacted continuously for 2~3 hours after the addition. The reaction was monitored by TLC until the spots of the raw material (4-hydroxylbenzaldehyde) disappeared, the solid produced by the reaction was filtered, dried and weighted 19 Kg (yield: 90%).

$^1$H NMR (400 MHz, DMSO-d$_6$): δ 6.88 (d, 2H, J=8.4 Hz), 7.18-7.27 (m, 4H), 7.76 (d, 2H, J=8.4 Hz), 8.46 (s, 1H), 10.11 (s, 1H).

Step 2: The product obtained in step 1 and 200 L dichloromethane were added to a 500 L reaction tank and were dissolved under stirring, 22 Kg triethylamine, 1.8 Kg 4-dimethylamino-pyridine (DMAP) were added at room temperature, 50 L dichloromethane solution with 20 Kg 3-nitrobenzoyl chloride dissolved were added drop by drop, the mixture was reacted continuously for 2~3 hours after the addition and monitored by TLC until the spots of the raw material (the product obtained from step 1) disappeared. The pH was adjusted to 4~6 by 2M hydrochloric acid, the solution was settled into layers, the organic phase was collected, the water phase was extracted by dichloromethane (30 L×2 times), the organic phases were combined and then washed 1 time with brine, dried over anhydrous sodium sulfate, filtered and evaporated to dryness under reduced pressure, the crude product was recrystallized in anhydrous ethanol, filtered and dried to obtain 19 Kg imine IXa (yield: 59%).

$^1$H NMR (400 MHz, DMSO-d$_6$): δ 7.23 (t, 2H, J=8.8 Hz), 7.31-7.35 (m, 2H), 7.49 (d, 2H, J=8.4 Hz), 7.90 (t, 1H, J=8.0 Hz), 8.03 (d, 2H, J=8.4 Hz), 8.52-8.58 (m, 2H), 8.65 (s, 1H), 8.78 (s, 1H).

Example 2

Preparation of 5-(4-fluorophenyl)-5-hydroxy-6-methoxy-6-oxo-hexanoic acid (IIIa)

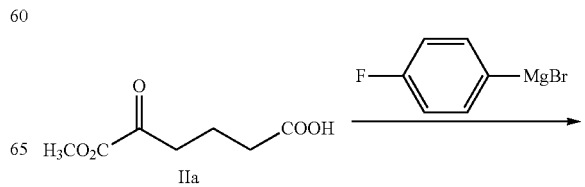

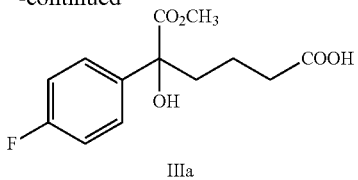

IIIa 100 g (0.563 mol) 6-methoxy-5,6-dioxo-hexanoic acid (compound IIa) and 300 mL tetrahydrofuran were added to a 3 L reaction flask, the mixture was protected under nitrogen and was dissolved under stirring, the temperature was decreased to −20° C.~−10° C., 1M solution of 4-fluorophenyl magnesium bromide in THF (1.4 L, 1.4 mol) was added slowly drop by drop, the temperature was kept for the reaction for 1~2 hours after the addition. The reaction was monitored by TLC until the spots of the raw material (compound IIa) disappeared.

A solution of 25% aqueous ammonium chloride (60 g ammonium chloride dissolved in 180 mL water) was added at the temperature of −20° C.~0° C. and was stirred for 5 minutes, then the pH was adjusted to 3~5 by 4M hydrochloric acid at the temperature of 0° C.~30° C., then 600 mL n-heptane was added and stirred for 5 minutes, the solution was settled into layers, the organic phase was collected, the water phase was extracted with ethyl acetate (140 mL×2 times), the organic phases were combined and then washed 2 times with saturated salt water, dried over anhydrous sodium sulfate, filtered and evaporated to dryness under reduced pressure, the crude product was recrystallized in toluene, filtered and dried to obtain 64.6 g compound IIIa (HPLC purity: 93.2%; yield: 39.6%).

$^1$H NMR (DMSO-d$_6$): 1.33-1.43 (m, 2H), 1.89-1.96 (m, 1H), 1.99-2.04 (m, 1H), 2.15 (t, 2H, J=7.6 Hz), 3.61 (s, 3H), 5.99 (s, 1H), 7.12-7.17 (m, 2H), 7.47-7.51 (m, 2H), 12.02 (s, 1H); MS (m/z): 269 [M–H]$^−$.

Example 3

Preparation of (Z)-5-(4-fluorophenyl)-6-methoxy-6-oxo-hex-4-enoic acid (IVa)

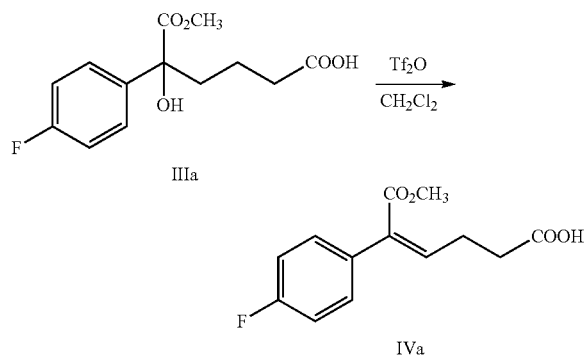

64.0 g (0.221 mol) 5-(4-fluorophenyl)-5-hydroxy-6-methoxy-6-oxo-hexanoic acid (compound IIIa) and 300 mL dichloromethane were added to a 500 mL reaction flask, the mixture was dissolved under stirring and was protected under nitrogen, the temperature was decreased, 65.6 g (0.233 mol) triflic anhydride was added at the temperature of 5° C.~15° C., then the reaction mixture was refluxed for 1~2 hours and monitored by TLC until the spots of the raw material (compound IIIa) disappeared.

The temperature was decreased, 100 mL water was added at the temperature of 5° C.~15° C. to quench the reaction, the solution was settled into layers, the organic phase was collected, the water phase was extracted with dichloromethane (60 mL×2 times), the organic phases were combined and then washed 3 times with saturated salt water, dried over anhydrous sodium sulfate, filtered and evaporated to dryness under reduced pressure to obtain 54.4 g compound IVa (HPLC purity: 95.6%; yield: 93.4%).

$^1$H NMR (DMSO-d$_6$): 2.42 (t, 2H, J=7.3 Hz), 2.56 (q, 2H, J=7.3 Hz), 3.74 (s, 3H), 6.27 (t, 1H, J=7.4 Hz), 7.18 (t, 2H, J=8.8 Hz), 7.32-7.36 (m, 2H), 12.19 (s, 1H).

Example 4

Preparation of (Z)-5-(4-fluorophenyl)-6-hydroxy-hex-4-enoic acid (V)

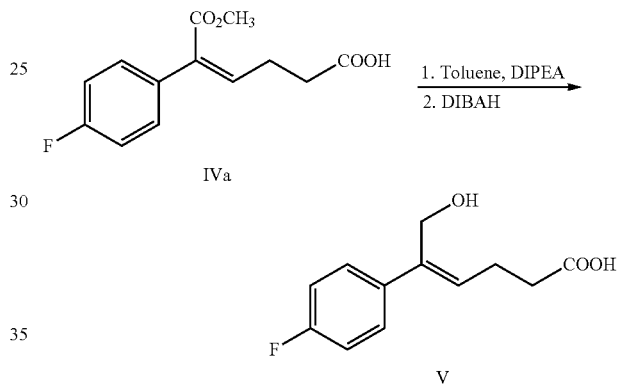

54.0 g (0.205 mol) (Z)-5-(4-fluorophenyl)-6-methoxy-6-oxo-hex-4-enoic acid (compound IVa) and 240 mL toluene were added to a 1 L reaction flask, the mixture was dissolved under stirring and was protected under nitrogen, 31.0 g (0.240 mol) diisopropylethylamine was added and was dissolved under stirring, the temperature was decreased to −20° C.~−15° C., 382.0 g (0.673 mol) DIBAH toluene solution (25%) was added slowly drop by drop, the temperature was kept for the reaction for 20~40 minutes after the addition. The reaction was monitored by TLC until the raw material (compound IVa) reacted completely.

Below the temperature of 15° C., the reaction mixture was added slowly to aqueous sodium hydroxide (72.2 g sodium hydroxide dissolved in 300 mL water) drop by drop, then the solution was stirred for 30 minutes; settled into layers, the water phase was collected, the water phase was extracted with dichloromethane (60 mL×2 times), the dichloromethane phase was discarded. The pH of the water phase was adjusted to 1~2 with 4M hydrochloric acid below the temperature of 25° C., 240 mL ethyl acetate was added, the solution was stirred for 5 minutes then was settled into layers, the organic phase was collected, and the water phase was extracted with ethyl acetate (100 mL×3 times). The organic phases were combined and washed 2 times with saturated salt water, dried over anhydrous sodium sulfate, filtered and evaporated to dryness under reduced pressure, the crude product was recrystallized in toluene, filtered and dried to obtain 36.4 g compound V (HPLC purity: 96.3%; yield: 76.4%).

¹H NMR (DMSO-d₆): 2.38 (t, 2H, J=7.1 Hz), 2.47 (q, 2H, J=7.0 Hz), 4.34 (s, 2H), 4.75 (br s, 1H), 5.78 (t, 1H, J=7.2 Hz), 7.13 (t, 2H, J=8.9 Hz), 7.45-7.48 (m, 2H), 12.13 (br s, 1H).

Example 5

Preparation of (Z)-5-(4-fluorophenyl)-6-(3-nitrobenzoyloxy)hex-4-enoic acid

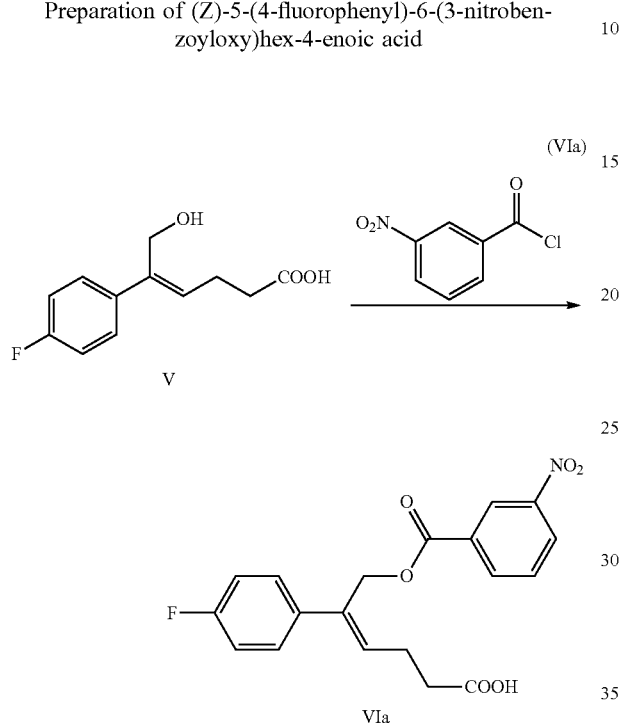

Example 6

Preparation of [(Z)-2-(4-fluorophenyl)-6-oxo-6-[(4S)-2-oxo-4-phenyl-oxazolidin-3-yl]hex-2-enyl]3-nitrobenzoate (VIIIa)

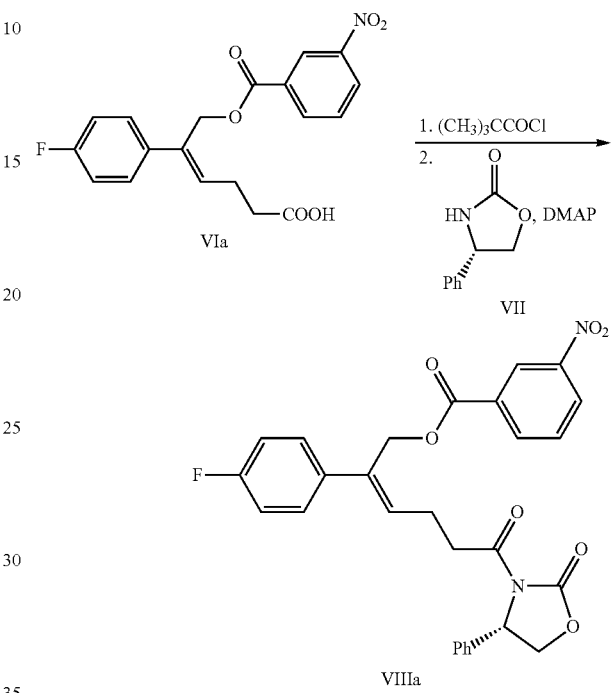

18.0 g (0.077 mol) (Z)-5-(4-fluorophenyl)-6-hydroxyhex-4-enoic acid (compound V) and 60 mL N,N-dimethylacetamide were added to a 250 mL reaction flask, the mixture was dissolved under stirring and was protected under nitrogen, the temperature was decreased, 31.2 g (0.168 mol) 3-nitrobenzoyl chloride was added at the temperature of −5° C.~5° C., then the reaction mixture was reacted for 5~6 hours at the temperature of −5° C.~5° C. and monitored by TLC until the spots of the raw material (compound V) disappeared.

At the temperature of 0~10° C., aqueous pyridine (13.0 g pyridine dissolved in 30 mL water) was added and stirred for 30 minutes, then at the temperature of 0~10° C., aqueous imidazole (22.5 g imidazole dissolved in 50 mL water) was added, stirred for 1~2 hours, then the solution was extracted with 120 mL ethyl acetate and settled into layers, the organic phase was collected, and the water phase was extracted with ethyl acetate (20 mL×3 times), the organic phases were combined, and the organic phase was washed with water, the pH was adjusted to 3~5 with 2M hydrochloric acid, then the organic phase was washed 1 time with saturated salt water, dried over anhydrous sodium sulfate, filtered and evaporated to dryness under reduced pressure to obtain 24.0 g compound VIa (HPLC purity: 92.6%; yield: 77.0%).

¹H NMR (DMSO-d₆): 2.45 (t, 2H, J=7.1 Hz), 2.59 (q, 2H, J=7.3 Hz), 5.36 (s, 2H), 6.09 (t, 1H, J=7.4 Hz), 7.18 (t, 2H, J=8.8 Hz), 7.51-7.54 (m, 2H), 7.80 (t, 1H, J=7.8 Hz), 8.23 (d, 1H, J=7.8 Hz), 8.46-8.48 (m, 2H), 12.17 (s, 1H).

24.0 g (0.060 mol) (Z)-5-(4-fluorophenyl)-6-(3-nitrobenzoyloxy)-hex-4-enoic acid (compound VIa) and 100 mL dichloromethane were added to a 250 mL reaction flask, the mixture was dissolved under stirring and was protected under nitrogen. 8.9 g (0.074 mol) pivaloyl chloride was added. At room temperature, 15.6 g (0.154 mol) triethylamine was added slowly drop by drop, the reaction mixture was reacted for 3~4 hours at room temperature after the addition. Then 7.8 g (0.048 mol) (S)-4-phenyl-2-oxazolidinone (compound VII) and 2.2 g (0.018 mol) 4-dimethylaminopyridine were added and reacted at room temperature for 3~4 hours. The reaction was monitored by TLC until the spots of the raw material (compound VIa) disappeared.

The pH was adjusted to 4~6 with 2M hydrochloric acid, the solution was settled into layers, the organic phase was collected and the water phase was extracted with dichloromethane (30 mL×2 times), the organic phases were combined. Aqueous imidazole (11.1 g imidazole dissolve in 30 mL water) was added and stirred for 1~2 hours, then was washed 1 time with saturated salt water, dried over anhydrous sodium sulfate, filtered and evaporated to dryness under reduced pressure. The crude product was recrystallized in toluene, filtered and dried to obtain 25.3 g compound VIIIa (HPLC purity: 95.1%; yield: 78.0%).

¹H NMR (DMSO-d₆): 2.59 (q, 2H, J=7.2 Hz), 3.00-3.18 (m, 2H), 4.15 (dd, 1H, J=8.8, 3.6 Hz), 4.72 (t, 1H, J=8.7 Hz), 5.29 (d, 1H, J=13.2 Hz), 5.32 (d, 1H, J=13.2 Hz), 5.45 (dd, 1H, J=8.6, 3.6 Hz), 6.05 (t, 1H, J=7.5 Hz), 7.17 (t, 2H, J=8.9 Hz), 7.26-7.36 (m, 5H), 7.46-7.50 (m, 2H), 7.76-7.80 (m, 1H), 8.19-8.21 (m, 1H), 8.45-8.47 (m, 2H).

Example 7

Preparation of the Compound of Formula VIIIa

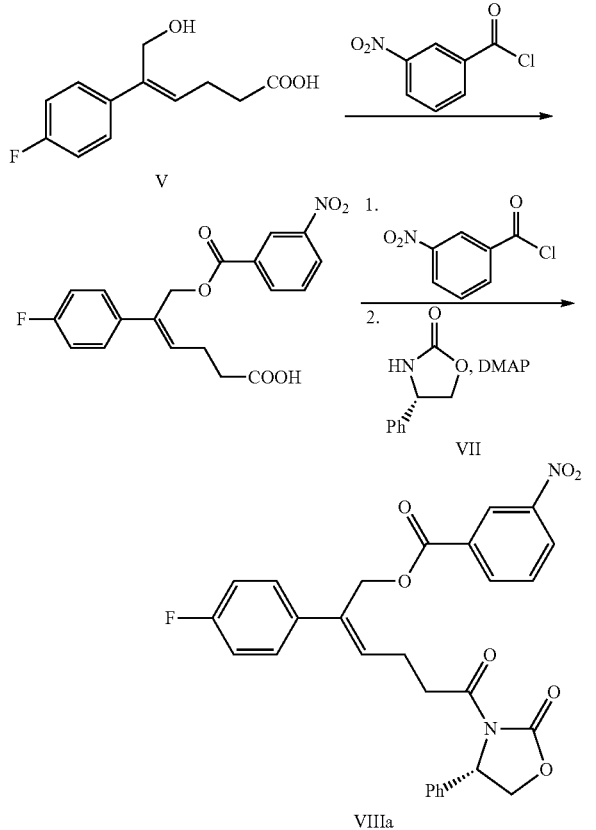

Step 1: 18 g (0.080 mol) (Z)-5-(4-fluorophenyl)-6-hydroxy-hex-4-enoic acid (compound V) and 90 mL N,N-dimethylacetamide were added to a 250 mL reaction flask, the mixture was dissolved under stirring and was protected under nitrogen. 17.8 g (0.096 mol) 3-nitrobenzoyl chloride was added at 25° C.~30° C., the temperature was kept for the reaction for 2 hours, the reaction was determined to be complete by HPLC, the reaction mixture was retained to be used.

Step 2: 180 mL dichloromethane and 16.3 g (0.088 mol) 3-nitrobenzoyl chloride were added to a 500 mL reaction flask and were protected under nitrogen, 32.4 g (0.32 mol) triethylamine was added drop by drop at the temperature of 25° C.~30° C., then the reaction mixture of step 1 was added drop by drop at the temperature of 25° C.~30° C. (the mixture was added within 1~2 hours), then the temperature was kept for the reaction for 5 minutes after the addition, then 11.75 g (0.072 mol) (S)-4-phenyl-2-oxazolidinone and 4.4 g (0.036 mol) 4-dimethylamino-pyridine were added, the temperature was kept for the reaction for 6~7 hours, the reaction was determined to be complete by HPLC.

90 mL water was added to the reaction mixture, the solution was settled into layers, the organic phase was collected and the water phase was extracted with dichloromethane (50 mL×2 times), the organic phases were combined. The pH of the organic phase was adjusted to 4~6 with 2M hydrochloric acid, then the organic phase was washed with 90 mL water until it is neutral, then aqueous imidazole (27 g imidazole dissolved in 50 mL water) was added, stirred for 30 minutes and settled into layers, the organic phase was collected and was washed with saturated salt water, dried over anhydrous sodium sulfate, filtered and evaporated to dryness under reduced pressure. The crude product was recrystallized in the mixed solvent of ethyl acetate/petroleum ether (2/3), filtered and dried to obtain 30 g compound VIIIa (HPLC purity: 97.5%; yield: 74.0%).

Example 8

Preparation of [(Z,5R)-5-[(S)-(4-fluoroanilino)-[4-(3-nitrobenzoyl)oxyphenyl]methyl]-2-(4-fluorophenyl)-6-oxo-6-[(4S)-2-oxo-4-phenyl-oxazolidin-3-yl]hex-2-enyl]3-nitrobenzoate (XIa)

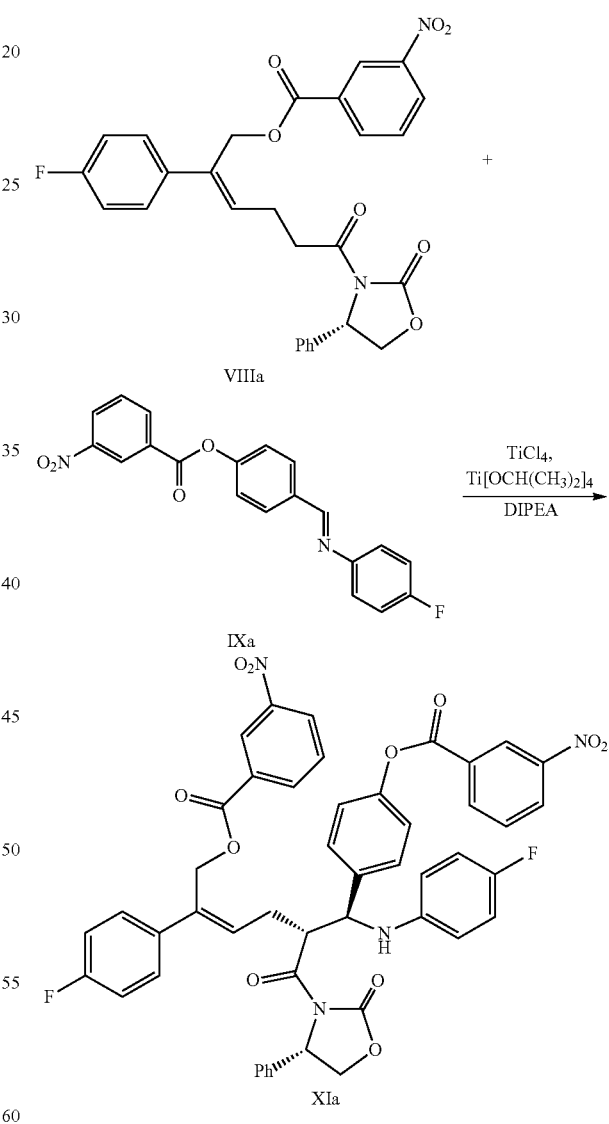

80 mL dichloromethane and 10.5 g (0.055 mol) titanium tetrachloride were added to a 250 mL reaction flask and were protected under nitrogen, the temperature was decreased, 5.2 g (0.018 mol) titanium isopropylate was added drop by drop at the temperature of −5° C.~0° C., then the solution was stirred for 30 minutes at the temperature of −5° C.~0° C. to obtain titanium reagent. 25.0 g (0.046 mol) compound of formula VIIIa, 18.3 g (0.050 mol) imine of formula IXa and 350 mL dichloromethane were added to a 1 L reaction flask and were dissolved under stirring, 14.3 g (0.111 mol) diisopropylethylamine was added and stirred, the temperature was decreased, the titanium reagent was added slowly drop by drop at the temperature of −25° C.~−20° C., then the mixture was reacted for 1~2 hours at the temperature of −25° C.~−20° C., the reaction was monitored by HPLC until the content of the raw material (compound VIIIa) was <5%.

30 mL acetic acid was added drop by drop at the temperature of −25° C.~−20° C. and stirred for 5 minutes; 150 mL sulfuric acid (2M) was added drop by drop below 10° C. and stirred for 10 minutes; the solution was settled into layers, the organic phase was collected, the water phase was extracted with dichloromethane (25 mL×2 times), the organic phases were combined and washed 3 times with saturated salt water, dried over anhydrous sodium sulfate, filtered and evaporated to dryness under reduced pressure. The crude product was recrystallized in toluene, filtered and dried to obtain 21.4 g compound XIa (HPLC purity: 95.3%; yield: 50.4%).

$^1$H NMR (DMSO-d$_6$): 2.38-2.45 (m, 1H), 2.56-2.64 (m, 1H), 4.11 (dd, 1H, J=8.8, 4.7 Hz), 4.62-4.75 (m, 3H), 5.15 (s, 2H), 5.51 (dd, 1H, J=8.5, 4.6 Hz), 5.98 (t, 1H, J=7.4 Hz), 6.34 (d, 1H, J=9.8 Hz), 6.58-6.62 (m, 2H), 6.80 (t, 2H, J=8.9 Hz), 7.13-7.28 (m, 9H), 7.45-7.48 (m, 2H), 7.54 (d, 2H, J=8.5 Hz), 7.79 (t, 1H, J=7.9 Hz), 7.91 (t, 1H, J=8.0 Hz), 8.18 (d, 1H, J=7.8 Hz), 8.43-8.49 (m, 3H), 8.57-8.60 (m, 1H), 8.74 (t, 1H, J=1.8 Hz); MS (m/z): 883 [M+H]$^+$.

Example 9

Preparation of the Compound of Formula XIa

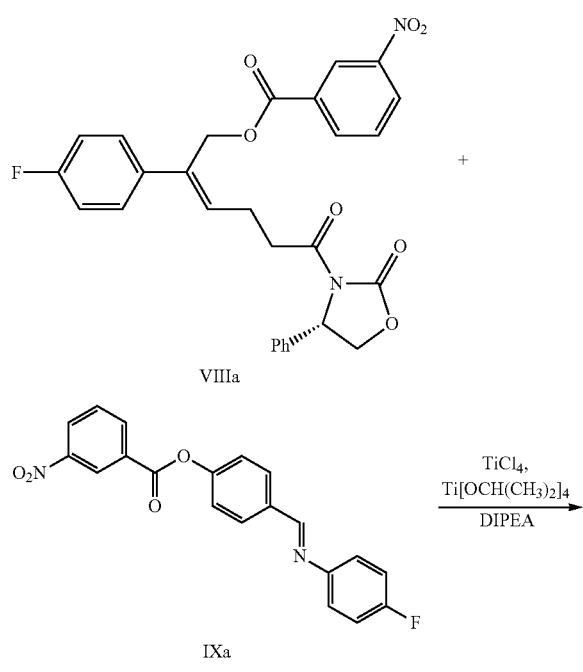

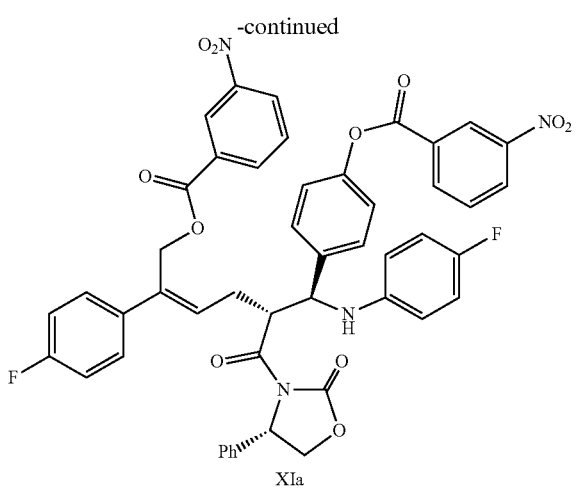

150 mL dichloromethane and 13.2 g (0.069 mol) titanium tetrachloride were added to a 500 mL reaction flask, were protected under nitrogen and were stirred, the temperature was decreased, 60 mL dichloromethane solution with 6.6 g (0.023 mol) titanium isopropylate dissolved was added drop by drop at the temperature of −5° C.~0° C., then the solution was stirred for 30 minutes at the temperature of −5° C.~0° C. to obtain titanium reagent. 30 g (0.058 mol) compound of formula VIIIa, 23.2 g (0.064 mol) imine of formula IXa and 900 mL dichloromethane were added to a 2 L reaction flask and were protected under nitrogen and were dissolved under stirring, 19.5 g diisopropylethylamine was added, the temperature was decreased, the titanium reagent prepared above was added slowly drop by drop at the temperature of −75° C.~−70° C., the addition was terminated within about 2 hours, then the reaction mixture was reacted for 5 minutes at the temperature of −75° C.~−70° C. and monitored by HPLC until the spots of the raw material (compound VIIIa) disappeared.

A solution of 135 mL 20% trifluoroacetic acid in dichloromethane was added quickly below the temperature of −70° C. and was stirred for 1 minute; 240 mL aqueous sulfuric acid (2M) was added quickly drop by drop below −30° C., then the solution was stirred and was warmed to room temperature; the solution was settled into layers, the organic phase was collected, the water phase was extracted with dichloromethane (100 mL×2 times), the organic phases were combined and washed with saturated salt water until it is neutral, dried over anhydrous sodium sulfate, filtered and evaporated to dryness under reduced pressure to obtain crude product. The crude product was recrystallized in the mixed solvent of ethyl acetate/petroleum ether (1/1), filtered and dried to obtain 35 g compound XIa (HPLC purity: 98.9%; yield: 68.7%).

Example 10

Preparation of (3R,4S)-4-[4-(3-nitrobenzoyloxy)phenyl]-3-[3-(4-fluorophenyl)-4-(3-nitrobenzoyloxy)but-2(Z)-enyl]-1-(4-fluorophenyl)azetidin-2-one (XIIa), (3R,4S)-4-(4-hydroxyphenyl)-3-[3-(4-fluorophenyl)-4-(3-nitrobenzoyloxy)but-2(Z)-enyl]-1-(4-fluorophenyl)azetidin-2-one (XIIIa), (3R,4S)-4-(4-trimethylsilyloxyphenyl)-3-[3-(4-fluorophenyl)-4-(3-nitrobenzoyloxy)but-2(Z)-enyl]-1-(4-fluorophenyl)azetidin-2-one (XIVa)

21.0 g (0.025 mol) compound of formula XIa and 200 mL toluene were added to a 500 mL reaction flask, the mixture was stirred and heated, 18.4 g (0.090 mol) N,O-bis(trimethylsilyl)acetamide (BSA) was added at the temperature of 50° C.~60° C., then reacted for 2 hours at this temperature; then 1.0 g (0.003 mol) tetrabutylammonium fluoride trihydrate was added at the temperature of 50° C.~60° C. and reacted for 2~3 hours at that temperature. The reaction was monitored by HPLC until the content of the raw material (compound XIa) was <1.0%.

The temperature was decreased below 25° C., 50 mL ice water was added drop by drop and stirred for 10 minutes, then 180 mL n-heptane was added and stirred continuously for 30 minutes, the solid was precipitated and filtered, and the filtrate was settled into layers, the organic phase was

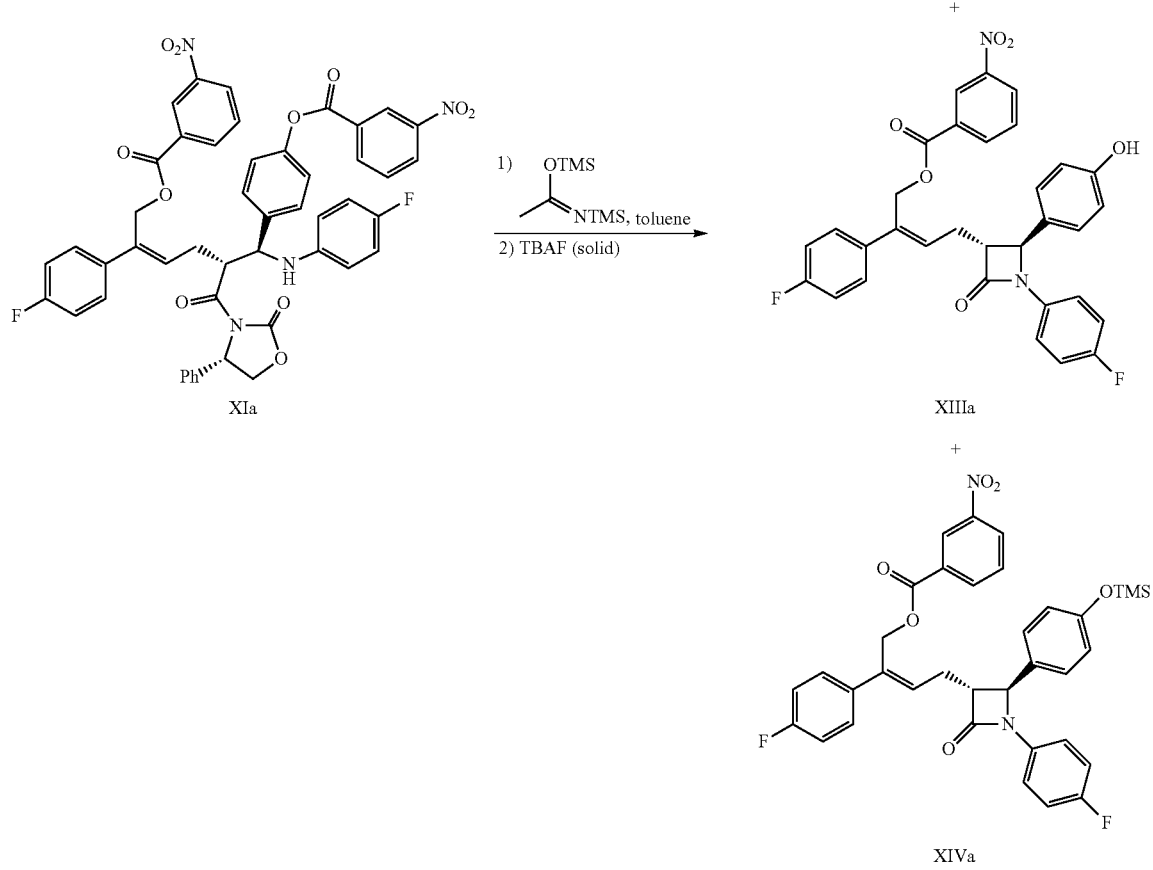

collected, the water phase was extracted with toluene (15 mL×2 times), the organic phases were combined and were concentrated to dry under vacuum, a mixture was obtained. A few of the mixture was taken to be separated to obtain three products, i.e. compounds XIIa, XIIIa, XIVa.

Compound XIIa: $^1$H NMR (400 MHz, DMSO-d$_6$): 2.91-3.08 (m, 2H), 3.41 (td, 1H, J=8.5, 2.1 Hz), 5.14 (d, 1H, J=2.0 Hz), 5.42 (d, 1H, J=13.1 Hz), 5.46 (d, 1H, J=13.1 Hz), 6.17 (t, 1H, J=7.5 Hz), 7.13-7.26 (m, 6H), 7.35 (d, 2H, J=8.5 Hz), 7.48-7.53 (m, 4H), 7.78 (t, 1H, J=8.0 Hz), 7.91 (t, 1H, J=8.0 Hz), 8.21 (d, 1H, J=7.8 Hz), 8.44-8.47 (m, 2H), 8.51 (d, 1H, J=7.9 Hz), 8.56-8.59 (m, 1H), 8.76 (t, 1H, J=1.7 Hz); MS (m/z): 720 [M+H]$^+$, 742 [M+Na]$^+$.

Compound XIIIa: $^1$H NMR (400 MHz, DMSO-d$_6$): 2.85-2.98 (m, 2H), 3.30 (td, 1H, J=8.5, 2.2 Hz), 4.92 (d, 1H, J=2.2 Hz), 5.40 (d, 1H, J=13.1 Hz), 5.44 (d, 1H, J=13.1 Hz), 6.13 (t, 1H, J=7.5 Hz), 6.73 (d, 2H, J=8.5 Hz), 7.12 (t, 2H, J=8.8 Hz), 7.16-7.21 (m, 6H), 7.47-7.50 (m, 2H), 7.79 (td, 1H, J=7.7, 0.9 Hz), 8.21 (d, 1H, J=7.8 Hz), 8.45-8.47 (m, 2H), 9.52 (s, 1H); MS (m/z): 571 [M+H]$^+$.

Compound XIVa: $^1$H NMR (400 MHz, CDCl$_3$): 0.28 (s, 9H), 2.97-3.01 (m, 2H), 3.30 (td, 1H, J=7.9, 2.2 Hz), 4.72 (d, 1H, J=2.1 Hz), 5.37 (s, 2H), 6.07 (t, 1H, J=7.6 Hz), 6.83 (d, 2H, J=8.5 Hz), 6.94 (t, 2H, J=8.6 Hz), 7.03 (t, 2H, J=8.6 Hz), 7.20 (d, 2H, J=8.5 Hz), 7.24-7.28 (m, 2H), 7.35-7.38 (m, 2H), 7.61 (t, 1H, J=8.0 Hz), 8.23 (d, 1H, J=7.8 Hz), 8.38-8.41 (m, 1H), 8.75 (t, 1H, J=1.7 Hz); MS (m/z): 643 [M+H]$^+$.

Example 11

Preparation of (3R,4S)-4-(4-hydroxyphenyl)-3-[3-(4-fluorophenyl)-4-hydroxy-but-2(Z)-enyl]-1-(4-fluorophenyl)azetidin-2-one (I)

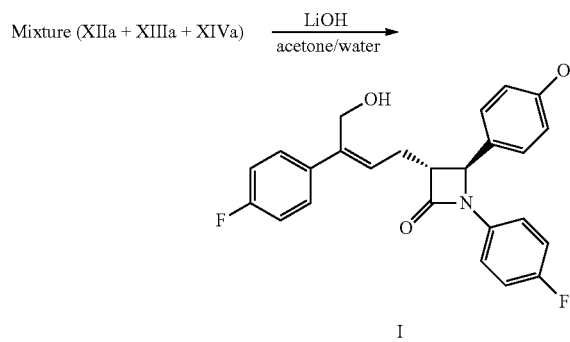

The mixture of the compounds of formula XIIa, XIIIa XIVa obtained in example 10 and 90 mL acetone were added to a 250 mL reaction flask and were dissolved under stirring, 23 mL (0.069 mol) aqueous lithium hydroxide (3M) was added at room temperature and the reaction mixture was reacted for 2~3 hours under stirring and monitored by TLC until the spots of the raw material (compounds XIIa, XIIIa XIVa) disappeared.

The pH was adjusted to 4~6 by 2M hydrochloric acid at room temperature, then the solution was concentrated under vacuum (30~40° C.) to small volume, 100 mL ethyl acetate was added and stirred for 5 minutes, the solution was settled into layers, the organic phase was collected, the water phase was extracted with ethyl acetate (20 mL×2 times), the organic phases were combined, aqueous sodium hydrogen carbonate (3.8 g sodium hydrogen carbonate dissolved in 40 mL water) was added and stirred for 30 minutes, the solution was settled into layers. The pH of the organic phase was adjusted to about 6 with 2M hydrochloric acid, settled into layers, the organic phase was washed 1 time with saturated salt water, dried over anhydrous sodium sulfate, filtered, the filtrate was concentrated to dry under reduced pressure. The residue was purified by column chromatography, recrystallized twice in the mixed solvent of ethyl acetate and n-heptane, filtered and dried to obtain 4.3 g compound I (HPLC purity: 99.2%; yield: 44.7% calculated according to the feeding amount of compound XIa of example 10).

$^1$H NMR (400 MHz, DMSO-d$_6$): δ 2.71-2.84 (m, 2H), 3.23 (td, 1H, J=6.4, 2.0 Hz), 4.40 (d, 2H, J=5.3 Hz), 4.87 (t, 1H, J=5.3 Hz), 4.94 (d, 1H, J=2.1 Hz), 5.80 (t, 1H, J=7.5 Hz), 6.74 (d, 2H, J=8.5 Hz), 7.11-7.17 (m, 4H), 7.20-7.25 (m, 4H), 7.39-7.43 (m, 2H), 9.50 (s, 1H); MS (m/z): 422 [M+H]$^+$.

Example 12

Preparation of 5-(4-fluorophenyl)-5-hydroxy-6-methoxy-6-oxo-hexanoic acid (IIIa)

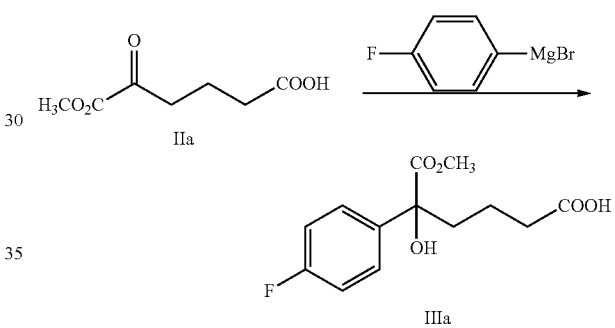

60 Kg (337.9 mol) 6-methoxy-5,6-dioxo-hexanoic acid (compound IIa) and 180 L tetrahydrofuran were added to a 2000 L reaction tank, the mixture was protected under nitrogen and dissolved under stirring, the temperature was decreased to −20° C.~−10° C., 1M solution of 4-fluorophenyl magnesium bromide in THF (800 L, 800 mol) was added slowly drop by drop and the temperature was kept for the reaction for 1~2 hours after the addition. The reaction was monitored by TLC until the spots of the raw material (compound IIa) disappeared.

A solution of 25% aqueous ammonium chloride (30 Kg ammonium chloride dissolved in 90 L water) was added at the temperature of −20° C.~0° C. and was stirred for 5 minutes, then the pH was adjusted to 3~5 with 4M hydrochloric acid at the temperature of 0° C.~30° C., then 400 L n-heptane was added and stirred for 5 minutes, the solution was settled into layers, the organic phase was collected, the water phase was extracted with ethyl acetate (80 L×2 times), the organic phases were combined and were washed 2 times with saturated salt water, dried over anhydrous sodium sulfate, filtered and evaporated to dryness under reduced pressure. The crude product was recrystallized in toluene, filtered and dried to obtain 45.6 Kg compound IIIa (HPLC purity: 70.8%; yield: 35.4%).

$^1$H NMR (DMSO-d$_6$): 1.33-1.43 (m, 2H), 1.89-1.96 (m, 1H), 1.99-2.04 (m, 1H), 2.15 (t, 2H, J=7.6 Hz), 3.61 (s, 3H), 5.99 (s, 1H), 7.12-7.17 (m, 2H), 7.47-7.51 (m, 2H), 12.02 (s, 1H); MS (m/z): 269 [M−H]$^−$.

Example 13

Preparation of (Z)-5-(4-fluorophenyl)-6-methoxy-6-oxo-hex-4-enoic acid (IVa)

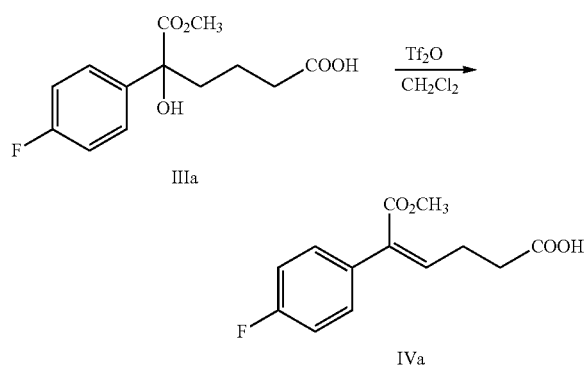

40.0 Kg (104.9 mol) 5-(4-fluorophenyl)-5-hydroxy-6-methoxy-6-oxo-hexanoic acid (compound IIIa) and 200 L dichloromethane were added to a 300 L reaction tank, the mixture was dissolved under stirring and was protected by nitrogen, the temperature was decreased, 31.2 Kg (110.6 mol) triflic anhydride was added at the temperature of 5~15° C., then the reaction mixture was refluxed for 1~2 hours and monitored by TLC until the spots of the raw material (compound IIIa) disappeared.

The temperature was decreased, the reaction was stopped by adding 50 L water under the temperature of 5° C.~15° C., stirred for 5 minutes and settled into layers, the organic phase was collected, the water phase was extracted with dichloromethane (40 L×2 times), the organic phases were combined and was washed 3 times with saturated salt water, dried over anhydrous sodium sulfate, filtered and evaporated to dryness under reduced pressure to obtain 25.2 Kg compound IVa (HPLC purity: 86.3%; yield: 82.3%).

$^1$H NMR (DMSO-$d_6$): 2.42 (t, 2H, J=7.3 Hz), 2.56 (q, 2H, J=7.3 Hz), 3.74 (s, 3H), 6.27 (t, 1H, J=7.4 Hz), 7.18 (t, 2H, J=8.8 Hz), 7.32-7.36 (m, 2H), 12.19 (s, 1H).

Example 14

Preparation of (Z)-5-(4-fluorophenyl)-6-hydroxy-hex-4-enoic acid (V)

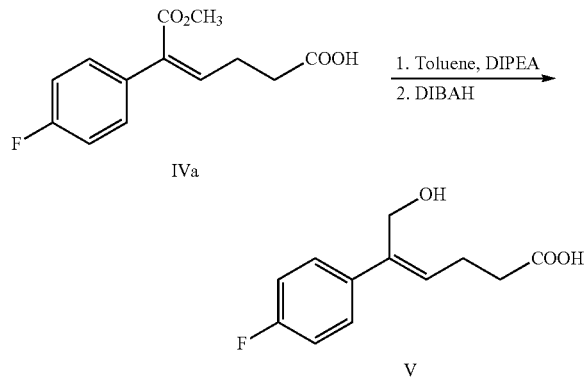

25.0 Kg (85.6 mol) (Z)-5-(4-fluorophenyl)-6-methoxy-6-oxo-hex-4-enoic acid (compound IVa) and 100 L toluene were added to a 500 L reaction tank, the mixture was dissolved under stirring and were protected by nitrogen, 13.0 Kg (100.8 mol) diisopropylethylamine was added, stirred for 5 minutes. The temperature was decreased to -20° C.~-15° C., 159.7 Kg (281.2 mol) DIBAH toluene solution (25%) was added slowly drop by drop and the temperature was kept for the reaction for 20~40 minutes after the addition. The reaction was monitored by TLC until the raw material (compound IVa) was reacted completely.

The reaction mixture was added slowly drop by drop to aqueous sodium hydroxide (30.2 Kg sodium hydroxide dissolved in 140 L water) below the temperature of 15° C. and was stirred for 30 minutes. The solution was settled into layers, the water phase was collected and extracted with 50 L dichloromethane, the dichloromethane phase was discarded, the pH of the water phase was adjusted to 1~2 below 25° C. with 6M hydrochloric acid, 100 L ethyl acetate was added and stirred for 5 minutes. The solution was settled into layers, the organic phase was collected, the water phase was extracted with ethyl acetate (40 L×3 times), the organic phases were combined and washed 2 times with saturated salt water, dried over anhydrous sodium sulfate, filtered and evaporated to dryness under reduced pressure. The crude product was recrystallized in toluene, filtered and dried to obtain 15.0 Kg compound V (HPLC purity: 92.1%; yield: 72.0%).

$^1$H NMR (DMSO-$d_6$): 2.38 (t, 2H, J=7.1 Hz), 2.47 (q, 2H, J=7.0 Hz), 4.34 (s, 2H), 4.75 (br s, 1H), 5.78 (t, 1H, J=7.2 Hz), 7.13 (t, 2H, J=8.9 Hz), 7.45-7.48 (m, 2H), 12.13 (br s, 1H).

Example 15

Preparation of (Z)-5-(4-fluorophenyl)-6-(3-nitrobenzoyloxy)hex-4-enoic acid (VIa)

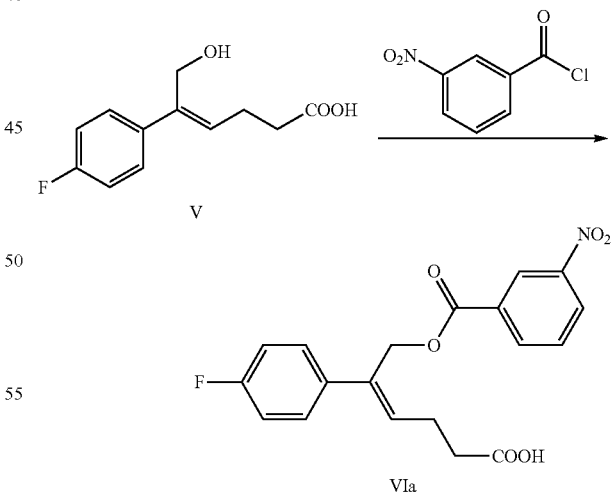

15.0 Kg (61.7 mol) (Z)-5-(4-fluorophenyl)-6-hydroxy-hex-4-enoic acid (compound V) and 50 L N,N-dimethylacetamide were added to a 300 L reaction tank, the mixture was dissolved under stirring and were protected by nitrogen. The temperature was decreased to -5° C.~5° C., 24.9 Kg (134.2 mol) 3-nitrobenzoyl chloride was added and the temperature was kept for the reaction for 5~6 hours. The reaction was monitored by TLC until the spots of the raw material (compound V) disappeared.

Aqueous pyridine was added (10.4 Kg pyridine dissolved in 30 L water) at the temperature of 0° C.~10° C. and was stirred for 30 minutes. Then aqueous imidazole (18.0 Kg imidazole dissolved in 50 L water) was added at the temperature of 0° C.~10° C. and was stirred for 1~2 hours, then 100 L ethyl acetate was added and was stirred for 5 minutes. The solution was settled into layers, the organic phase was collected, the water phase was extracted with ethyl acetate (20 L×3 times), the organic phases were combined and were washed with water, the pH was adjusted to 3~5 with 2M hydrochloric acid, washed 1 time with saturated salt water, dried over anhydrous sodium sulfate, filtered and evaporated to dryness under reduced pressure to obtain 20.2 Kg compound VIa (HPLC purity: 85.6%; yield: 75.2%).

$^1$H NMR (DMSO-$d_6$): 2.45 (t, 2H, J=7.1 Hz), 2.59 (q, 2H, J=7.3 Hz), 5.36 (s, 2H), 6.09 (t, 1H, J=7.4 Hz), 7.18 (t, 2H, J=8.8 Hz), 7.51-7.54 (m, 2H), 7.80 (t, 1H, J=7.8 Hz), 8.23 (d, 1H, J=7.8 Hz), 8.46-8.48 (m, 2H), 12.17 (s, 1H).

Example 16

Preparation of [(Z)-2-(4-fluorophenyl)-6-oxo-6-[(4S)-2-oxo-4-phenyl-oxazolidin-3-yl]hex-2-enyl]3-nitrobenzoate (VIIIa)

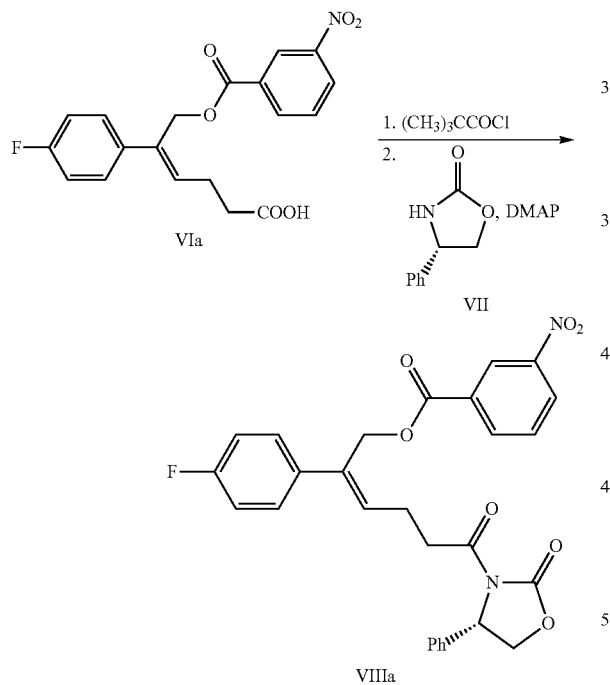

20.0 Kg (45.9 mol) (Z)-5-(4-fluorophenyl)-6-(3-nitrobenzoyloxy)-hex-4-enoic acid (compound VIa) and 100 L dichloromethane were added to a 300 L reaction tank, the mixture was dissolved under stirring and were protected by nitrogen. 6.8 Kg (56.4 mol) pivaloyl chloride was added. At room temperature, 12.0 Kg (118.8 mol) triethylamine was added slowly drop by drop, the reaction mixture was reacted at room temperature for 3~4 hours after the addition, then 6.0 Kg (36.8 mol) (S)-4-phenyl-2-oxazolidinone (compound VII) and 1.7 Kg (13.9 mol) 4-dimethylaminopyridine were added and reacted at room temperature for 4~5 hours. The reaction was monitored by TLC until the spots of the raw material (compound VIa) disappeared.

The pH was adjusted to 4~6 with 2M hydrochloric acid, the solution was settled into layers, the organic phase was collected, and the water phase was extracted with dichloromethane (25 L×2 time), the organic phases were combined, aqueous imidazole (8.6 Kg imidazole dissolved in 30 L water) was added and stirred for 2~3 hours, then was washed 1 time with saturated salt water, dried over anhydrous sodium sulfate, filtered and evaporated to dryness under reduced pressure. The crude product was recrystallized in toluene, filtered and dried to obtain 15.2 Kg compound VIIIa (HPLC purity: 91.7%; yield: 58.6%).

$^1$H NMR (DMSO-$d_6$): 2.59 (q, 2H, J=7.2 Hz), 3.00-3.18 (m, 2H), 4.15 (dd, 1H, J=8.8, 3.6 Hz), 4.72 (t, 1H, J=8.7 Hz), 5.29 (d, 1H, J=13.2 Hz), 5.32 (d, 1H, J=13.2 Hz), 5.45 (dd, 1H, J=8.6, 3.6 Hz), 6.05 (t, 1H, J=7.5 Hz), 7.17 (t, 2H, J=8.9 Hz), 7.26-7.36 (m, 5H), 7.46-7.50 (m, 2H), 7.76-7.80 (m, 1H), 8.19-8.21 (m, 1H), 8.45-8.47 (m, 2H).

Example 17

Preparation of [(Z,5R)-5-[(S)-(4-fluoroanilino)-[4-(3-nitrobenzoyl)oxyphenyl]methyl]-2-(4-fluorophenyl)-6-oxo-6-[(4S)-2-oxo-4-phenyl-oxazolidin-3-yl]hex-2-enyl]3-nitrobenzoate (XIa)

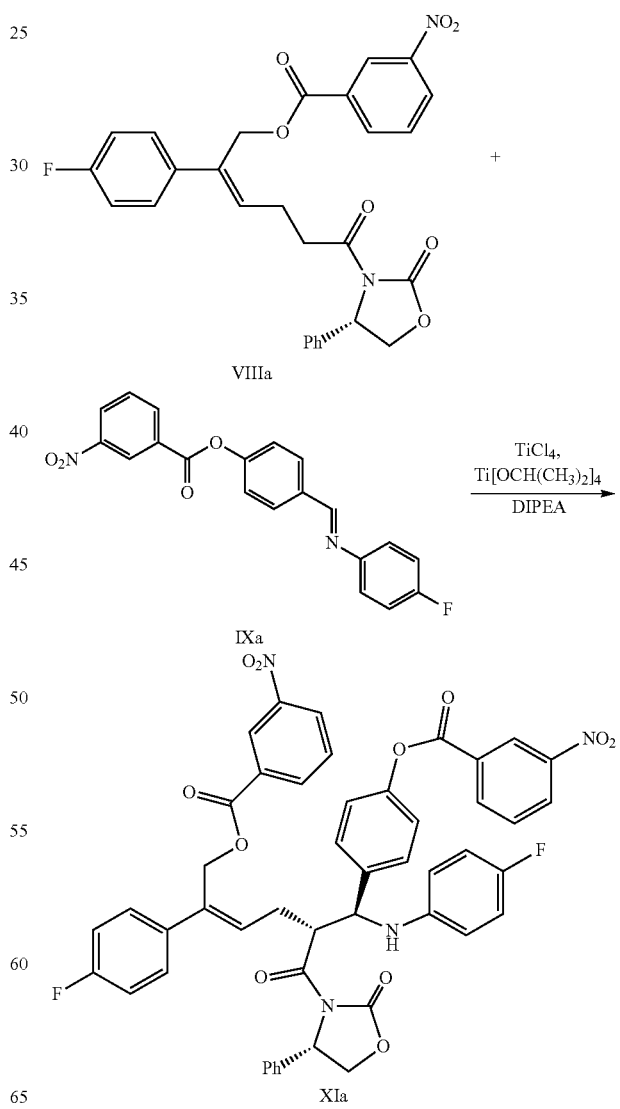

60 L dichloromethane and 6.0 Kg (31.6 mol) titanium tetrachloride were added to a 100 L reaction tank and were protected under nitrogen, stirred, the temperature was decreased, 3.0 Kg (10.6 mol) tetraisopropyl titanate was added at the temperature of −5° C.~0° C., then stirred for 30 minutes at the temperature of −5° C.~0° C. to obtain titanium reagent. 15.0 Kg (26.6 mol) compound of formula VIIIa, 10.6 Kg (29.1 mol) imine of formula IXa and 220 L dichloromethane were added to a 500 L reaction tank and were dissolved under stirring, 8.3 Kg (64.3 mol) diisopropylethylamine was added and stirred for 10 minutes, the temperature was decreased, the titanium reagent was added slowly drop by drop at the temperature of −25° C.~−20° C., the temperature was kept to react for 1~2 hours after the addition. The reaction was monitored by HPLC until the content of the raw material (compound VIIIa) was <5%.

18 L acetic acid was added at the temperature of −25° C.~−20° C., then was stirred for 5 minutes; 90 L sulfuric acid (2M) was added drop by drop below 10° C., then was stirred for 10 minutes. The solution was settled into layers, the organic phase was collected, and the water phase was extracted with 30 L dichloromethane. The organic phases were combined and washed 3 times with saturated salt water, dried over anhydrous sodium sulfate, filtered and evaporated to dryness under reduced pressure. The crude product was recrystallized in toluene, filtered and dried to obtain 12.3 Kg compound XIa (HPLC purity: 92.1%; yield: 48.4%).

$^1$H NMR (DMSO-$d_6$): 2.38-2.45 (m, 1H), 2.56-2.64 (m, 1H), 4.11 (dd, 1H, J=8.8, 4.7 Hz), 4.62-4.75 (m, 3H), 5.15 (s, 2H), 5.51 (dd, 1H, J=8.5, 4.6 Hz), 5.98 (t, 1H, J=7.4 Hz), 6.34 (d, 1H, J=9.8 Hz), 6.58-6.62 (m, 2H), 6.80 (t, 2H, J=8.9 Hz), 7.13-7.28 (m, 9H), 7.45-7.48 (m, 2H), 7.54 (d, 2H, J=8.5 Hz), 7.79 (t, 1H, J=7.9 Hz), 7.91 (t, 1H, J=8.0 Hz), 8.18 (d, 1H, J=7.8 Hz), 8.43-8.49 (m, 3H), 8.57-8.60 (m, 1H), 8.74 (t, 1H, J=1.8 Hz); MS (m/z): 883 [M+H]$^+$.

Example 18

Preparation of (3R,4S)-4-[4-(3-nitrobenzoyloxy) phenyl]-3-[3-(4-fluorophenyl)-4-(3-nitrobenzoyloxy) but-2(Z)-enyl]-1-(4-fluorophenyhazetidin-2-one (XIIa), (3R,4S)-4-(4-hydroxyphenyl)-3-[3-(4-fluorophenyl)-4-(3-nitrobenzoyloxy)but-2(Z)-enyl]-1-(4-fluorophenyhazetidin-2-one(XIIIa), (3R,4S)-4-(4-trimethylsilyloxyphenyl)-3-[3-(4-fluorophenyl)-4-(3-nitrobenzoyloxy)but-2(Z)-enyl]-1-(4-fluorophenyhazetidin-2-one(XIVa)

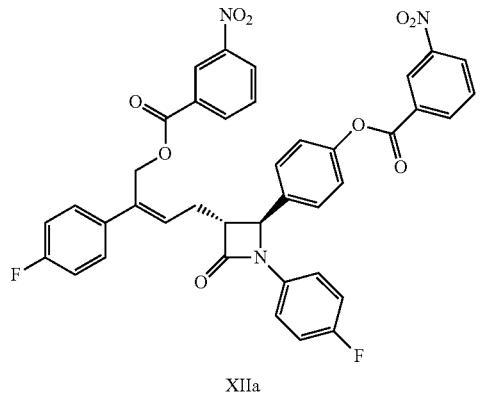

XIIa

+

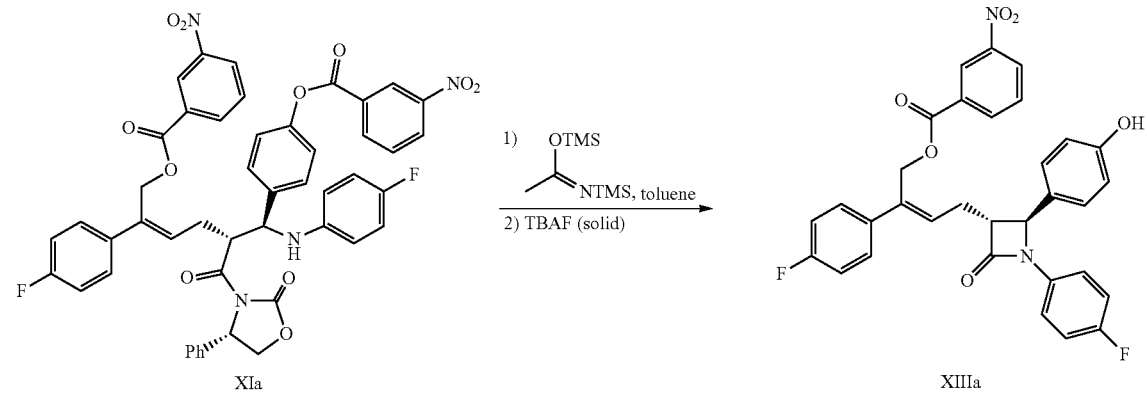

XIa

XIIIa

+

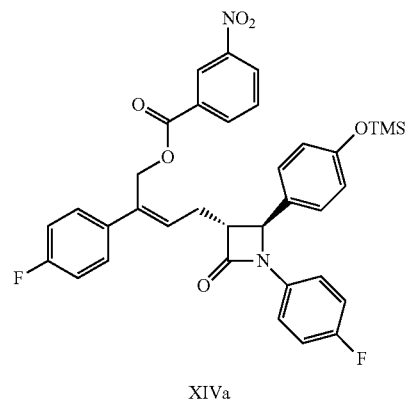

XIVa 12.0 Kg (12.5 mol) compound of formula XIa and 120 L toluene were added to a 300 L reaction tank and were stirred and heated, 10.2 Kg (50.0 mol) N,O-bis(trimethylsilyl)acetamide (BSA) was added at 50° C.~60° C., reacted for 2~3 hours at said temperature; then 0.6 Kg (1.9 mol) tetrabutylammonium fluoride trihydrate was added and the temperature was kept for the reaction for 2~3 hours. The reaction was monitored by HPLC until the content of the raw material (compound XIa) was <1.0%.

The temperature was decreased, 30 L ice water was added drop by drop below 25° C., the solution was stirred for 10 minutes, then 100 L n-heptane was added and stirred for 30 minutes, the solids were precipitated and filtered, the filtrate was settled into layers, the organic phase was collected, and the water phase was extracted with toluene (10 L×2 times). The organic phases were combined and were concentrated to dry under vacuum to obtain a mixture. A few of the mixture was taken to be separated to obtain three products, i.e. compound XIIa, XIIIa, XIVa.

Compound XIIa: $^1$H NMR (400 MHz, DMSO-$d_6$): 2.91-3.08 (m, 2H), 3.41 (td, 1H, J=8.5, 2.1 Hz), 5.14 (d, 1H, J=2.0 Hz), 5.42 (d, 1H, J=13.1 Hz), 5.46 (d, 1H, J=13.1 Hz), 6.17 (t, 1H, J=7.5 Hz), 7.13-7.26 (m, 6H), 7.35 (d, 2H, J=8.5 Hz), 7.48-7.53 (m, 4H), 7.78 (t, 1H, J=8.0 Hz), 7.91 (t, 1H, J=8.0 Hz), 8.21 (d, 1H, J=7.8 Hz), 8.44-8.47 (m, 2H), 8.51 (d, 1H, J=7.9 Hz), 8.56-8.59 (m, 1H), 8.76 (t, 1H, J=1.7 Hz); MS (m/z): 720 [M+H]$^+$, 742 [M+Na]$^+$.

Compound XIIIa: $^1$H NMR (400 MHz, DMSO-$d_6$): 2.85-2.98 (m, 2H), 3.30 (td, 1H, J=8.5, 2.2 Hz), 4.92 (d, 1H, J=2.2 Hz), 5.40 (d, 1H, J=13.1 Hz), 5.44 (d, 1H, J=13.1 Hz), 6.13 (t, 1H, J=7.5 Hz), 6.73 (d, 2H, J=8.5 Hz), 7.12 (t, 2H, J=8.8 Hz), 7.16-7.21 (m, 6H), 7.47-7.50 (m, 2H), 7.79 (td, 1H, J=7.7, 0.9 Hz), 8.21 (d, 1H, J=7.8 Hz), 8.45-8.47 (m, 2H), 9.52 (s, 1H); MS (m/z): 571 [M+H]$^+$.

Compound XIVa: $^1$H NMR (400 MHz, CDCl$_3$): 0.28 (s, 9H), 2.97-3.01 (m, 2H), 3.30 (td, 1H, J=7.9, 2.2 Hz), 4.72 (d, 1H, J=2.1 Hz), 5.37 (s, 2H), 6.07 (t, 1H, J=7.6 Hz), 6.83 (d, 2H, J=8.5 Hz), 6.94 (t, 2H, J=8.6 Hz), 7.03 (t, 2H, J=8.6 Hz), 7.20 (d, 2H, J=8.5 Hz), 7.24-7.28 (m, 2H), 7.35-7.38 (m, 2H), 7.61 (t, 1H, J=8.0 Hz), 8.23 (d, 1H, J=7.8 Hz), 8.38-8.41 (m, 1H), 8.75 (t, 1H, J=1.7 Hz); MS (m/z): 643 [M+H]$^+$.

Example 19

Preparation of (3R,4S)-4-(4-hydroxyphenyl)-3-[3-(4-fluorophenyl)-4-hydroxybut-2(Z)-enyl]-1-(4-fluorophenyl)azetidin-2-one (I)

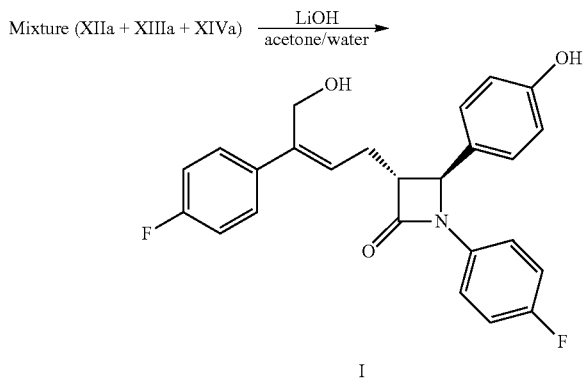

I

The mixture of compounds XIIa, XIIIa, XIVa obtained in example 18 and 50 L acetone were added to a 100 L reaction tank and were dissolved under stirring, 13 L (39.0 mol) aqueous lithium hydroxide (3M) was added at room temperature and was reacted for 0.5~1 hour under stirring. The reaction was monitored by TLC until the spots of the raw material (compound XIIa, XIIIa, XIVa) disappeared.

The pH was adjusted to 4~6 with 2M hydrochloric acid at room temperature, then the solution was concentrated under vacuum (at 30° C.~40° C.) to small volume, 60 L ethyl acetate was added and stirred for 5 minutes, then the solution was settled into layers, the organic phase was collected, the water phase was extracted with ethyl acetate (10 L×2 times). The organic phases were combined, aqueous sodium bicarbonate (2.0 Kg sodium bicarbonate dissolved in 20 L water) was added, stirred for 30 minutes, the solution was settled into layers, the pH of the organic phase was adjusted to about 6 with 2M hydrochloric acid, the solution was settled into layers, the organic phase was washed 1 time with saturated salt water, dried over anhydrous sodium sulfate, filtered, the filtrate was concentrated to dry under reduced pressure. The residue was purified by column chromatography, crystallized twice in the mixed solvent of ethyl acetate and n-heptane, filtered and dried to obtain 2.1 Kg compound I (HPLC purity: 98.9%; yield: 39.4% calculated according to the feeding amount of compound XIa of example 18).

$^1$H NMR (400 MHz, DMSO-$d_6$): δ 2.71-2.84 (m, 2H), 3.23 (td, 1H, J=6.4, 2.0 Hz), 4.40 (d, 2H, J=5.3 Hz), 4.87 (t, 1H, J=5.3 Hz), 4.94 (d, 1H, J=2.1 Hz), 5.80 (t, 1H, J=7.5 Hz), 6.74 (d, 2H, J=8.5 Hz), 7.11-7.17 (m, 4H), 7.20-7.25 (m, 4H), 7.39-7.43 (m, 2H), 9.50 (s, 1H); MS (m/z): 422 [M+H]$^+$.

The invention claimed is:

1. A compound of formula V:

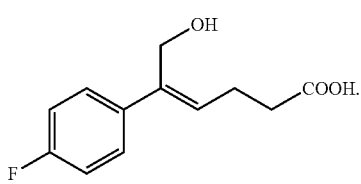

2. A method for preparing the compound of claim 1, comprising: selectively reducing the ester of formula IV to the alcohol of formula V under the action of a reducing agent:

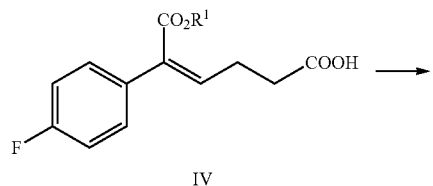

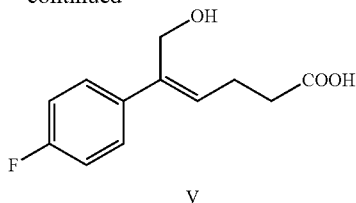

wherein $R^1$ is $C_1$-$C_6$ alkyl.

3. The method according to claim 2, wherein a solvent used in reducing the ester of formula IV to the alcohol of formula V is selected from dichloromethane, tetrahydrofuran, toluene or dioxane.

4. The method according to claim 2, wherein the reducing agent is diisobutylaluminium hydride (DIBAH).

5. The method according to claim 2, wherein a molar ratio of the compound of formula IV to the reducing agent is 1:2.5~5.0.

6. The method according to claim 1, wherein in the ester of formula IV, $R^1$ is methyl, ethyl or isopropyl.

7. The method according to claim 1, wherein a solvent used in reducing the ester of formula IV to the alcohol of formula V is toluene.

8. The method according to claim 1, wherein a molar ratio of the compound of formula IV to the reducing agent is 1:3.0~4.0.

* * * * *